(12) United States Patent  
Gellman

(10) Patent No.: US 6,660,010 B2
(45) Date of Patent: Dec. 9, 2003

(54) BONE ANCHOR PLACEMENT DEVICE WITH RECESSED ANCHOR MOUNT

(75) Inventor: Barry N. Gellman, North Eastern, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 139 days.

(21) Appl. No.: 09/738,378

(22) Filed: Dec. 15, 2000

(65) Prior Publication Data

US 2001/0027321 A1 Oct. 4, 2001

Related U.S. Application Data

(63) Continuation-in-part of application No. 09/309,816, filed on May 11, 1999, now Pat. No. 6,241,736, application No. 09/738,378, and a continuation-in-part of application No. 09/238,654, filed on Jan. 26, 1999, now Pat. No. 6,264,676.
(60) Provisional application No. 60/125,207, filed on Mar. 18, 1999, provisional application No. 60/085,113, filed on May 12, 1998, and provisional application No. 60/072,641, filed on Jan. 27, 1998.

(51) Int. Cl.[7] .............................................. A61B 17/58
(52) U.S. Cl. ...................................................... 606/104
(58) Field of Search ........................... 606/72, 73, 80, 606/99, 104, 232

(56) References Cited

U.S. PATENT DOCUMENTS 1,030,530 A    6/1912   Palmer
1,179,910 A    4/1916   Greenfield
1,417,669 A    5/1922   Langworthy (List continued on next page.)

FOREIGN PATENT DOCUMENTS

EP    0 241 240    10/1987
EP    0 558 993     9/1993
EP    0 599 772     6/1994

(List continued on next page.)

OTHER PUBLICATIONS

Benderev, "A modified percutaneous outpatient bladder neck suspension system." J. Urology 152: 2316–2320 (1994).
Hurson et al., "The use of spiked plastic washers in the repair of avulsed ligaments." Acta Orthop. Scand. 52: 23–26 (1981).

(List continued on next page.)

Primary Examiner—Eduardo C. Robert
(74) Attorney, Agent, or Firm—Testa, Hurwitz & Thibeault, LLP

(57) ABSTRACT

A bone anchor placement device includes a handle and a shaft extending in a distal direction from the handle. A head is disposed at a distal end of the shaft and a retractable anchor driver is disposed within the head. The recessed anchor mount is operable to advance from the head during placement of an anchor in to a supporting structure. The recessed anchor mount is operable to retract into the head during insertion of the placement device within a human body. The recessed anchor mount may include a push wire for advancing and retracting the retractable anchor mount.

8 Claims, 39 Drawing Sheets

U.S. PATENT DOCUMENTS

| | | |
|---|---|---|
| 2,200,120 A | 5/1940 | Nauth |
| 2,655,921 A | 10/1953 | Haboush |
| 2,707,783 A | 5/1955 | Sullivan |
| 3,388,847 A | 6/1968 | Kasulin |
| 3,593,903 A | 7/1971 | Vasillevich et al. |
| 3,892,232 A | 7/1975 | Neufeld |
| 3,953,896 A | 5/1976 | Treace |
| 3,971,271 A | 7/1976 | Wagner et al. |
| 4,159,716 A | 7/1979 | Borchers |
| 4,204,623 A | 5/1980 | Green |
| 4,422,567 A | 12/1983 | Haynes |
| 4,483,562 A | 11/1984 | Schoolman |
| 4,527,726 A | 7/1985 | Assell et al. |
| 4,537,185 A | 8/1985 | Stednitz |
| 4,576,167 A | 3/1986 | Noiles |
| 4,606,343 A | 8/1986 | Conta et al. |
| 4,632,100 A | 12/1986 | Somers et al. |
| 4,632,101 A | 12/1986 | Freedland |
| 4,635,634 A | 1/1987 | Santos |
| 4,664,305 A | 5/1987 | Blake, III et al. |
| 4,738,255 A | 4/1988 | Goble et al. |
| 4,739,751 A | 4/1988 | Sapega et al. |
| 4,784,137 A | 11/1988 | Kulik et al. |
| 4,856,385 A | 8/1989 | Ogilvie et al. |
| 4,870,957 A | 10/1989 | Goble et al. |
| 4,940,467 A | 7/1990 | Tronzo |
| 5,002,550 A | 3/1991 | Li |
| 5,019,078 A | 5/1991 | Perren et al. |
| 5,037,422 A | 8/1991 | Hayhurst et al. |
| 5,037,426 A | 8/1991 | Goble et al. |
| 5,040,715 A | 8/1991 | Green et al. |
| 5,052,607 A | 10/1991 | Dutton |
| 5,057,112 A | 10/1991 | Sherman et al. |
| 5,061,181 A | 10/1991 | Niznick |
| 5,064,434 A | 11/1991 | Haber |
| 5,067,956 A | 11/1991 | Buford, III et al. |
| 5,084,050 A | 1/1992 | Draenert |
| 5,100,417 A | 3/1992 | Cerier et al. |
| 5,102,421 A | 4/1992 | Anspach, Jr. |
| 5,116,338 A | 5/1992 | Poggie et al. |
| 5,141,520 A | 8/1992 | Goble et al. |
| 5,149,329 A | 9/1992 | Richardson |
| 5,180,382 A | 1/1993 | Frigg et al. |
| 5,190,543 A | 3/1993 | Schlapfer |
| 5,203,784 A | 4/1993 | Ross et al. |
| 5,217,462 A | 6/1993 | Asnis et al. |
| 5,224,946 A | 7/1993 | Hayhurst et al. |
| 5,258,016 A | 11/1993 | DiPoto et al. |
| 5,268,001 A | 12/1993 | Nicholson et al. |
| 5,289,963 A | 3/1994 | McGarry et al. |
| 5,328,077 A | 7/1994 | Lou |
| 5,370,662 A | 12/1994 | Stone et al. |
| 5,381,943 A | 1/1995 | Allen et al. |
| 5,411,506 A | 5/1995 | Goble et al. |
| 5,443,482 A | 8/1995 | Stone et al. |
| 5,464,407 A | 11/1995 | McGuire |
| 5,470,334 A | 11/1995 | Ross et al. |
| 5,520,696 A | 5/1996 | Wenstrom, Jr. |
| 5,520,700 A | 5/1996 | Beyar et al. |
| 5,522,843 A | 6/1996 | Zang |
| 5,544,664 A | 8/1996 | Benderev et al. |
| 5,573,548 A | 11/1996 | Nazre et al. |
| 5,591,207 A | 1/1997 | Coleman |
| 5,607,432 A | 3/1997 | Fucci |
| 5,611,515 A | 3/1997 | Benderev et al. |
| 5,674,247 A | 10/1997 | Sohn |
| 5,683,418 A | 11/1997 | Luscombe et al. |
| 5,690,677 A | 11/1997 | Schmieding et al. |
| 5,697,931 A | 12/1997 | Thompson |
| 5,702,397 A | 12/1997 | Goble et al. |
| 5,720,766 A | 2/1998 | Zang et al. |
| 5,725,529 A | 3/1998 | Nicholson et al. |
| 5,725,541 A * | 3/1998 | Anspach et al. ............ 606/151 |
| 5,735,849 A | 4/1998 | Baden et al. |
| 5,741,268 A * | 4/1998 | Schutz ........................ 606/104 |
| 5,755,726 A | 5/1998 | Pratt et al. |
| 5,782,862 A | 7/1998 | Bonutti |
| 5,807,403 A * | 9/1998 | Beyar et al. ................. 606/232 |
| 5,824,011 A | 10/1998 | Stone et al. |
| 5,842,478 A | 12/1998 | Benderev et al. |
| 5,851,219 A | 12/1998 | Goble et al. |
| 5,931,844 A * | 8/1999 | Thompson et al. ......... 606/144 |
| 5,948,001 A * | 9/1999 | Larsen ........................ 606/232 |
| 5,993,459 A * | 11/1999 | Larsen et al. ............... 606/104 |
| 6,039,686 A | 3/2000 | Kovac |
| 6,139,565 A | 10/2000 | Stone et al. |
| 6,273,893 B1 * | 8/2001 | McAllen et al. ............ 606/104 |
| 6,402,759 B1 * | 6/2002 | Strong et al. ............... 606/104 |

FOREIGN PATENT DOCUMENTS

| | | |
|---|---|---|
| EP | 0 686 373 | 6/1995 |
| FR | 95 11543 | 9/1995 |
| FR | 2 718 012 | 10/1995 |
| GB | 1044633 | 10/1966 |
| GB | 2268690 | 1/1994 |
| WO | 89/10096 | 11/1989 |
| WO | 92/16152 | 10/1992 |
| WO | 94 04080 | 3/1994 |
| WO | 95/15726 | 6/1995 |
| WO | 95/16399 | 6/1995 |
| WO | 96/06567 | 3/1996 |
| WO | WO 96/25887 | 8/1996 |
| WO | 96/28100 | 9/1996 |
| WO | WO 97/06731 | 2/1997 |
| WO | 97/13465 | 4/1997 |
| WO | 97/30638 | 8/1997 |
| WO | WO 97/30638 | 8/1997 |
| WO | WO 97/41792 | 11/1997 |
| WO | 98/12971 | 4/1998 |

OTHER PUBLICATIONS

Influence Inc.: Products: Incontinence (http://www.influencemedical.com/products) May 23, 2000.

International Search Report for PCT/US99/10275.

Mascio, Therapy of urinary stress incontinence in women: using Mitek® Gll Anchors, Mitek® Brochure, 1993.

O'Carroll et al., "A technique of medical ligament repair of the knee with cancellous screws and spiked washers." Injury 15: 99–104 (1983).

Parra et al. "Experience with a simplified technique for the treatment of female stress urinary incontinence." British J. Urology 66: 615–617 (1990).

Pederson et al., "Mitek® Anchor System: A new technique for Tenodesis and Ligamentous repair of the foot and ankle." J. Foot Surgery 30: 48–51 (1991).

Product Literature on ANCHORLOK®, Wright Medical Technology, Inc. 1995.

Product Literature on Influence In–Fast Bone Screw System, Apr. 24, 1998 from website: www.influencemedical.com/products/products.html.

Richmond et al., "Modification of the Bankart reconstruction with a suture anchor: Report of a new technique." Am. J. Sports Med. 19: 343–346 (1991).

Wolf et al., "Arthroscopic Bankart repair using suture anchors, operative techniques in orthopaedics."1(2): 187–191 (1991).

* cited by examiner

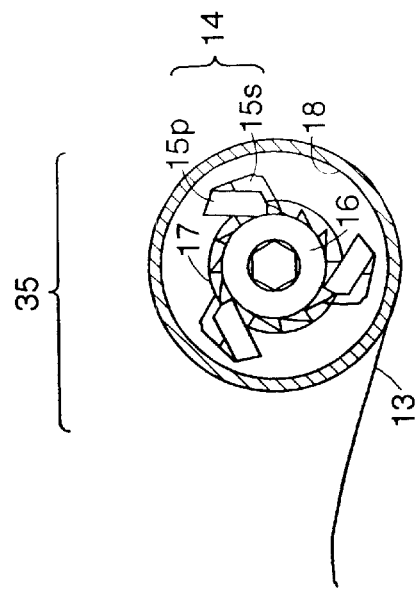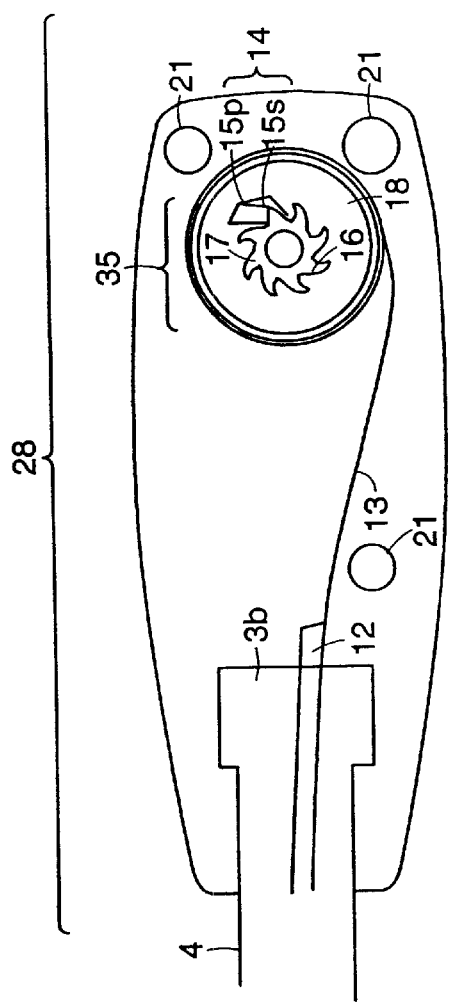
FIG. 4B
FIG. 4A

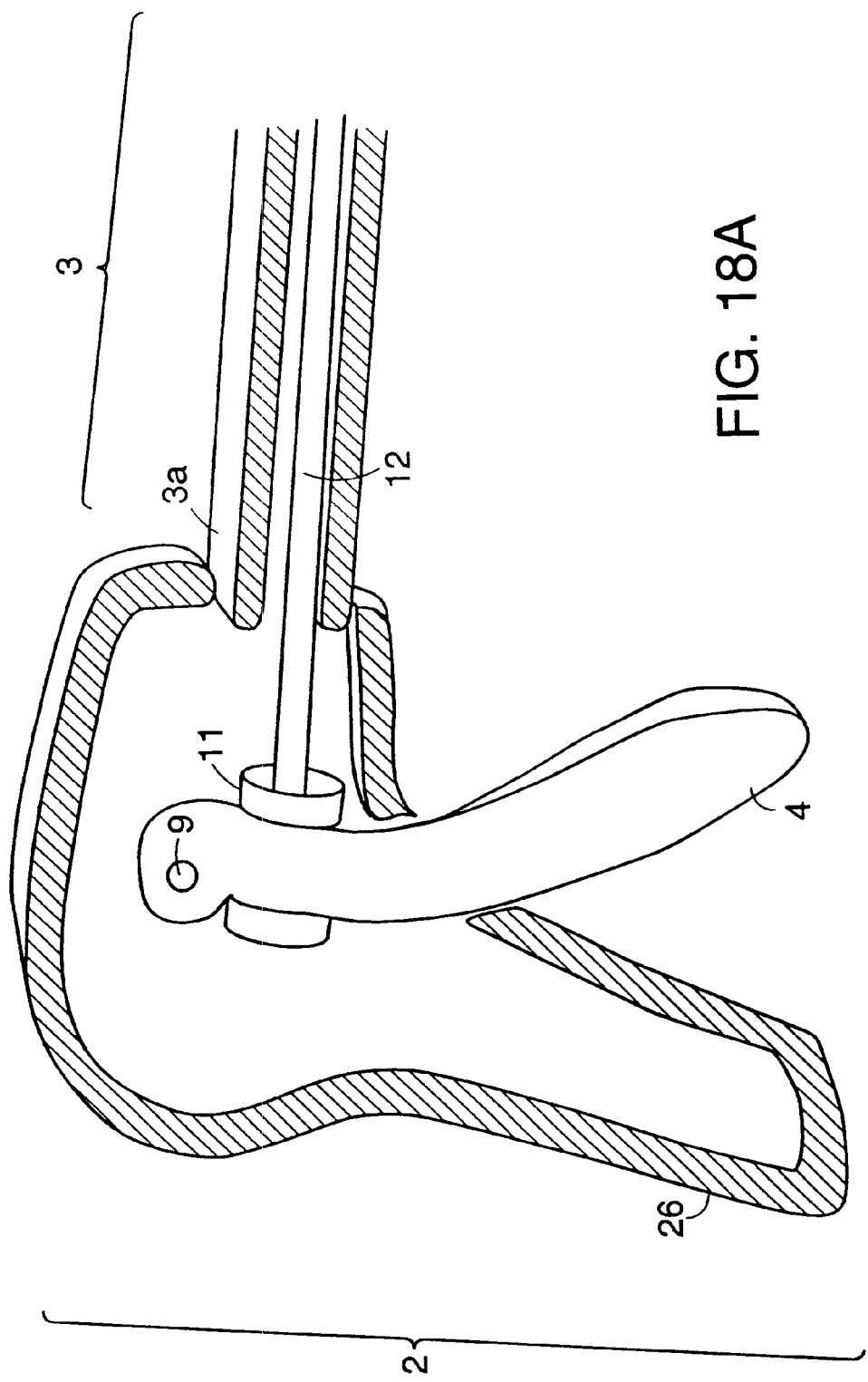

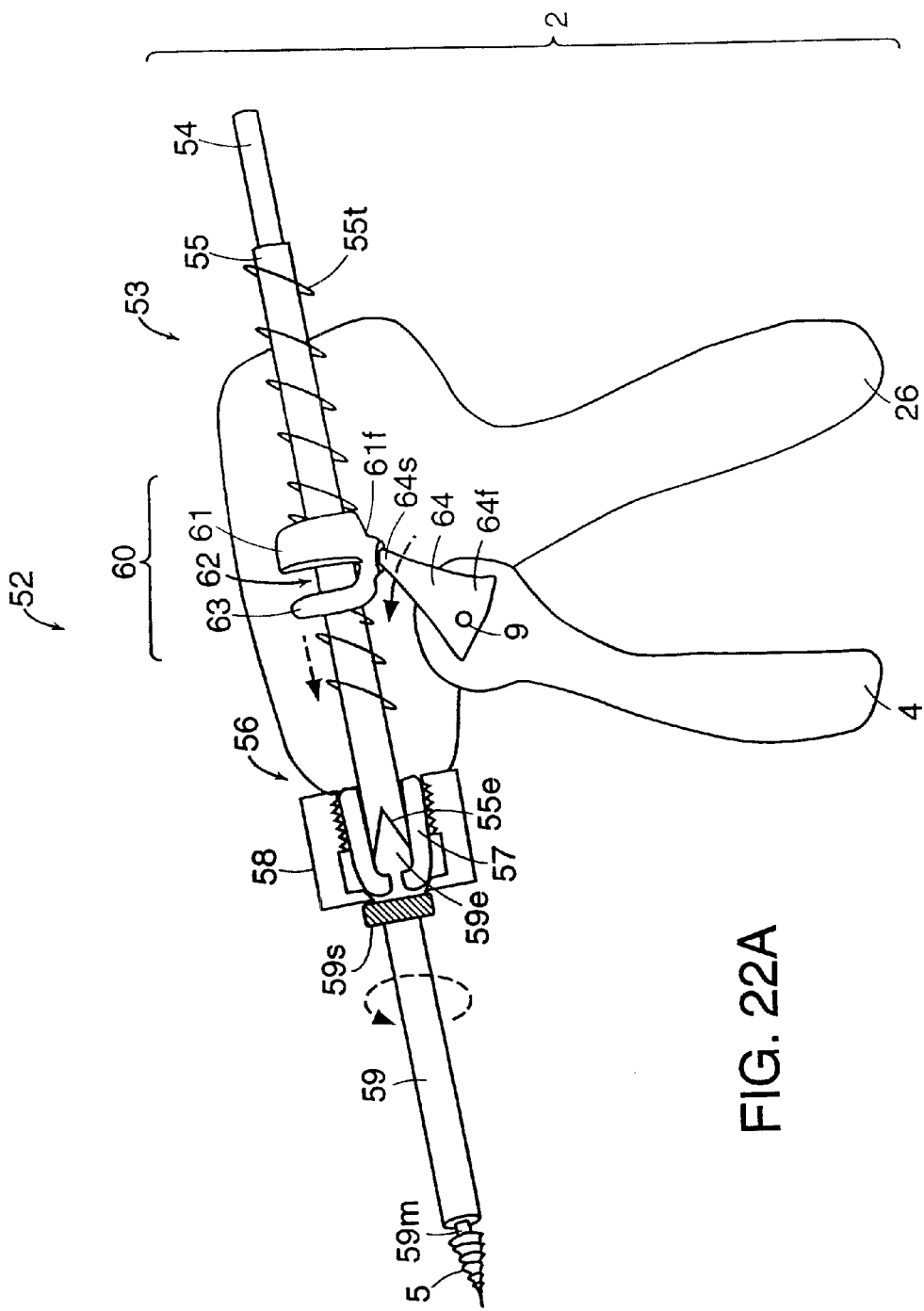

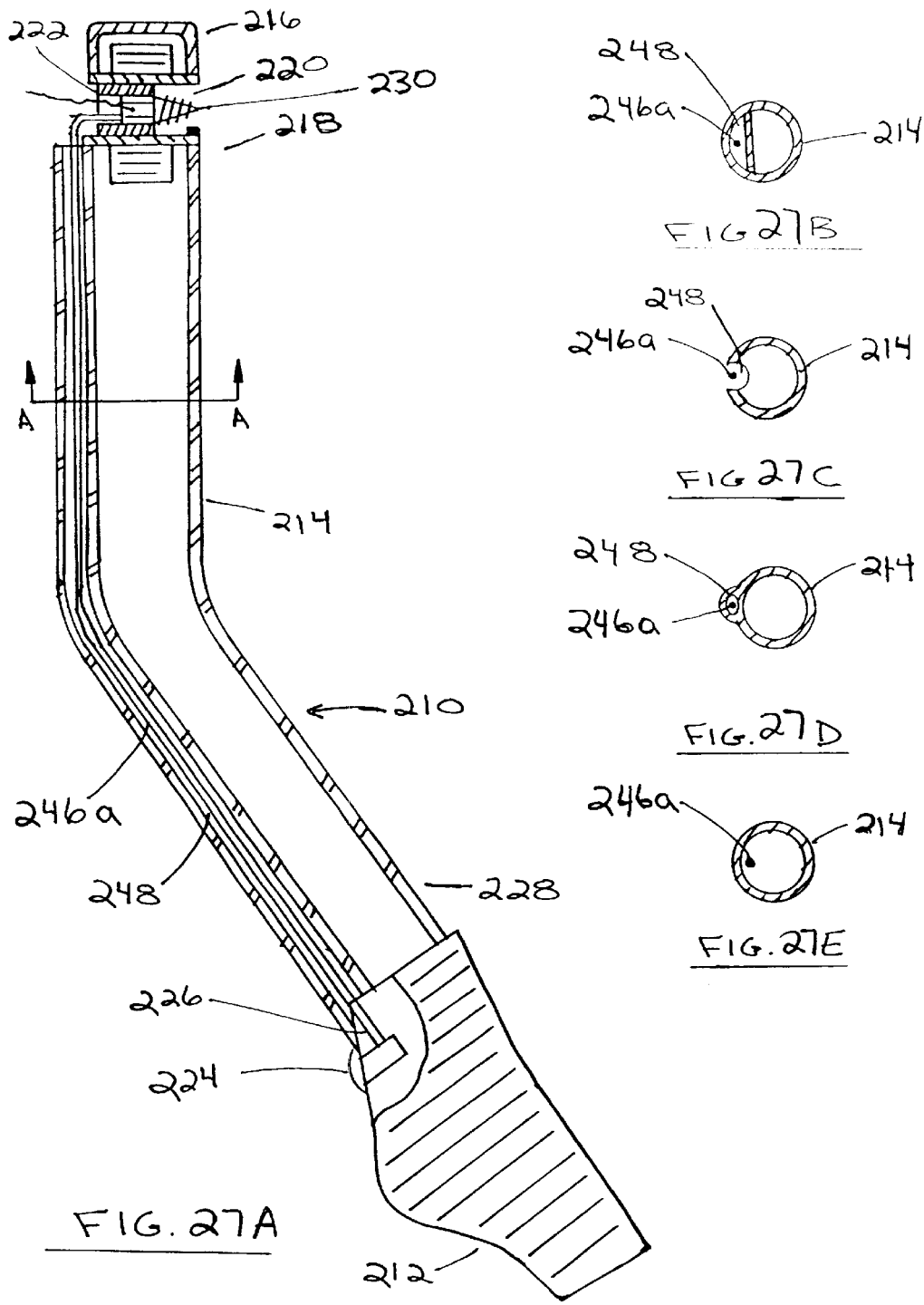

BONE ANCHOR PLACEMENT DEVICE WITH RECESSED ANCHOR MOUNT

CROSS-REFERENCE TO RELATED APPLICATIONS

This is a continuation-in-part of U.S. patent application Ser. No. 09/309,816, filed on May 11, 1999, now U.S. Pat. No. 6,246,736, which claims priority to U.S. Provisional Patent Application Ser. Nos. 60/085,113, filed May 12, 1998, and 60/125,207, filed Mar. 18, 1999. This is also a continuation-in-part of U.S. patent application Ser. No. 09/238,654, filed on Jan. 26, 1999, now U.S. Pat. No. 6,264,676, which claims priority to U.S. Provisional Patent Application Ser. No. 60/072,641, filed Jan. 27, 1998.

TECHNICAL FIELD

The invention relates generally to devices for placing bone anchors in bone, and in particular, to recessed bone anchor mounts used in connection with bone anchor drivers.

BACKGROUND INFORMATION

Urinary incontinence in women may be caused by urethral hypermobility, a condition in which the bladder neck and proximal urethra may rotate and descend in response to increases in intra-abdominal pressure. Hypermobility may be the result of aging, child delivery or conditions that weaken, stretch, or tear the muscles around the bladder, bladder neck and/or urethra. Urinary incontinence may also be caused by intrinsic sphincter deficiency (ISD), a condition in which the urethral sphincter does not coapt properly.

There are numerous approaches for treating urinary incontinence. In a bladder neck suspension procedure for treating hypermobility, sutures are placed around the muscle groups on either side of the urethra and are affixed to the pubic bone or other supporting structures to reposition and resuspend the proximal urethra. Also common are sling type operations, which may be performed to treat urethral hypermobility, intrinsic sphincter deficiency or both. In a sling type operation, a sling is placed under the urethra and bladder and is tensioned to elevate and stabilize the urethra, prevent excessive downward mobility, or compress the sphincter to treat intrinsic sphincter deficiency.

In these procedures, sutures are anchored to the supporting structures, such as the pubic bone, Cooper's ligament, or the rectus fascia. Bone anchor placement devices, such as bone anchor drivers, may be used to place bone anchors at selected insertion sites in the pubic bone. Sutures may then be attached to the bone anchors.

To reduce postoperative patient discomfort, transvaginal surgical procedures for bone anchor placement are preferred over percutaneous procedures, which require an incision in the abdominal wall (and sometimes the vaginal wall) to introduce a bone anchor placement device, and can be highly invasive and traumatic to the patient. In a transvaginal procedure, vaginal incisions are made and bone anchors or similar attachment devices are secured to the posterior side pelvic wall through the vaginal incision. While being guided to the desired locations, the anchor placement device passes through multiple layers of tissue. During this process, an unprotected bone anchor can catch, tear or scrape tissue, snap a surgeon's glove, or become dislodged.

It is desirable, therefore, to provide a protection mechanism for the bone anchor that prevents the sharp tip of the anchor from causing unintended tissue damage during passage of the anchor through tissue. At the same time, it is desirable that the head design for a bone anchor placement device be as compact as possible to minimize the necessary size of the vaginal incision through which the anchor placement device is inserted.

SUMMARY OF THE INVENTION

The present invention relates to manual bone anchor placement devices. The manual bone anchor placement devices disclosed herein are particularly useful in transvaginal methods of treating female urinary incontinence, although they can be used in other medical applications. The devices of the present invention are designed to permit rotational insertion of a bone anchor screw and to provide low cost alternatives to powered cannulated drills. The devices may be disposable or may be modular in nature, thereby allowing interchange of parts for reuse.

An advantage of the disclosed manual bone anchor placement devices is that they eliminate the need for a percutaneous incision to access an insertion area, although the devices can be used in a percutaneous procedure. A transvaginal approach to inserting a bone anchor screw into the pubic bone is far less invasive than a percutaneous procedure, thus a transvaginal procedure is far less traumatic for the patient.

An additional advantage of the disclosed manual bone anchor placement devices is that they seat a self-tapping bone anchor screw with a pre-attached suture. Since the bone anchor screw used with the disclosed devices is self-tapping and the suture is pre-attached, it is unnecessary for the physician to prebore a hole into the bone, remove the drill, introduce a seating device, seat the bone anchor screw, and then thread the suture. Single-step insertion of the bone anchor screw and suture not only reduces the total time required for the procedure, it also greatly reduces the possibility that the physician may lose access to the bored hole or seated bone anchor screw. Thus, the possible need to drill additional holes and/or seat additional bone anchor screws is reduced.

The manual bone anchor placement devices disclosed herein provide a mechanism to translate linear force exerted by a user on a lever into rotary force on a bone anchor screw. In one aspect of the invention, the manual bone anchor placement device includes a manually actuatable lever, a resilient element, a force translator, and a rotator. The force translator is coupled at its proximal end to the lever and at its distal end to the resilient element. The resilient element is coupled to the rotator. Linear force on the lever is transmitted through the force translator to the resilient element and from the resilient element to the rotator. The rotator rotates in response to this force. The device may further include a securing element coupled to the rotator that mates with a bone anchor screw and rotates when the rotator rotates, thereby applying a torque on the bone anchor screw and placing the bone anchor screw into bone.

In another aspect of the invention, the manual bone anchor placement device includes a manually actuatable lever, a force translator, a rack, and a rotator. The force translator includes a distal end and a proximal end, the proximal end receiving force from the lever, the distal end being coupled to the rack. The force translator transmits force to the rack, which moves linearly into an engaging position in response to this force. The rotator is positioned in close proximity to the rack for engagement with the rack when the rack moves into the engaging position. Engagement of the rotator by the rack causes the rotator to rotate. The device may further include a coupler coupled to the rotator that mates with a bone anchor screw and rotates when the rotator rotates, thereby placing the bone anchor screw into bone.

In another aspect of the invention, a manual bone anchor placement device is disclosed that includes a manually actuatable lever, a driver rod with threads, and a cup and washer positioned over the threads. The cup is coupled to the lever and moves axially along the driver rod upon actuation of the lever, engaging with the washer. When the cup and washer engage each other, linear force transmitted from the lever through the cup is translated to a rotary force on the driver rod, rotating the driver rod. The device may further include a coupling element for mating with a bone anchor screw and for rotating when the driver rod rotates to place the bone anchor screw into bone.

The present invention also relates to a self-tapping buttress-shaped bone anchor screw. The bone anchor screw of the present invention comprises a micropolished eyelet for receiving a suture. The eyelet may be circular, ellipsoidal, or teardrop shaped. The bone anchor screw described herein is designed to require less torque to seat and to minimize load on a pre-attached suture in comparison with known bone anchor screws.

Kits are also disclosed comprising any of: a molded flexible sleeve for enclosing a suture, a retaining clip for preventing the suture from slipping out of the sleeve, a buttress-shaped bone anchor screw comprising a micropolished eyelet for receiving a suture, and a suture which may, or may not, be pre-attached to the bone anchor screw. A collapsible, protective cover for a bone anchor screw is also disclosed.

In yet another aspect of the invention, the manual bone anchor placement device includes a head assembly, a recessed anchor mount movably disposed within the head assembly, and an actuation mechanism coupled to the recessed anchor mount. In various embodiments, the actuation mechanism can be a push wire or a pull wire, and the mechanism actuates the recessed anchor mount between a recessed position and an advanced position. The anchor mount can include an outer surface having at least one flat surface and the head assembly can have a core comprising a mating shape. Further, the manual bone anchor placement device can include a bone anchor releasably engaged to the anchor mount. In addition, the anchor mount can include a groove for accommodating a suture attached to the bone anchor.

In still another aspect of the invention, the manual bone anchor placement device includes a handle, a shaft extending in a distal direction from the handle, a head assembly disposed at a distal end of the shaft, a recessed anchor mount movably disposed within the head assembly, and an actuation mechanism coupled to the recessed anchor mount. In various embodiments, the actuation mechanism can be a push wire or a pull wire, and the mechanism actuates the recessed anchor mount between a recessed position and an advanced position. Further, the actuation mechanism can be situated within a channel disposed on the handle, an actuator disposed on the handle can operate the actuation mechanism, and the actuation mechanism may be manufactured of spring steel or nitinol. The anchor mount can include an outer surface having at least one flat surface and the head assembly can have a core comprising a mating shape. Further, the manual bone anchor placement device can include a bone anchor releasably engaged to the anchor mount. In addition, the anchor mount can include a groove for accommodating a suture attached to the bone anchor.

Still further, the manual bone anchor placement device can include a stop disposed within the head assembly, for example within the core. Alternatively, the stop can be located on the actuation mechanism.

These and other objects, along with advantages and features of the present invention herein disclosed, will become apparent through reference to the following description of embodiments of the invention, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention.

FIGS. 4A–4D show views of the head end of a wrap-around manual bone anchor placement device according to different embodiments of the invention. FIG. 4A shows a cross-sectional view of an embodiment where the rotator includes a floating pawl. FIG. 4B shows an enlarged cross-sectional view of a rotator that has three floating pawls. FIG. 4C shows a three-dimensional cut-away view of the head end of the shaft in an embodiment of the invention where the rotator has two floating pawls. FIG. 4D shows a three-dimensional cut-away view of the head end of the shaft in an embodiment of the invention where the rotator has a single floating pawl.

FIGS. 5A–5D show enlarged views of a securing element that has a hex-shaped recess in its mating portion for mating with a bone anchor screw with a hex-shaped shaft at its base. FIG. 5A is a perspective view of the securing element showing the hex-shaped recess. FIG. 5B is a cross-sectional view through the engaging portion of the securing element. FIG. 5C is a perspective side-view of the securing element. FIG. 5D is a view from the top of the securing element. FIG. 5E shows a bone anchor screw that has a hex-shaped shaft at its base. FIG. 5F shows a perspective view of a securing element whose mating portion has a hex-shaped protrusion. FIG. 5G shows a perspective side view of a securing element whose mating portion has a hex-shaped protrusion. FIG. 5H shows an enlarged view of a bone anchor screw with a hex-shaped recess at its base for mating with a securing element whose mating portion has a hex-shaped protrusion.

FIG. 6A shows a perspective view. FIG. 6B shows a side view. FIG. 6C shows a cross-sectional view.

FIG. 7A shows a perspective view. FIG. 7B shows a side view. FIG. 7C shows a cross-sectional view.

FIG. 8A shows a perspective view where the flat spring portion is slightly bent. FIG. 8B shows a side view of a flat spring portion that is slightly bent. FIG. 8C shows a perspective view where the flat spring portion is lying flat.

FIGS. 18A and 18B show a side view of a cross-section through the handle and proximal portion of the shaft in a rack and rotator manual bone anchor placement device according to one embodiment of the invention. FIG. 18A shows an action mechanism that transmits a pull force on a force translator. FIG. 18B shows an action mechanism that transmits a push force on a force translator.

FIG. 22A shows a cross-sectional sideview of a cup and washer manual bone anchor placement device according to one embodiment of the invention that includes a cup and washer rotary force mechanism.

FIG. 23A shows a cross-sectional view of a driver rod with grooves to interface with protrusions on a washer. FIG. 23B shows a cross-sectional view of a washer with corresponding protrusions to interface with the grooves in the driver rod. FIG. 23C shows a perspective side view of a cup and washer assembly on a driver rod in which the washer is in a "free-floating" or non-engaged position. FIG. 23D shows a perspective sideview of a cup and washer assembly in which the washer is in an engaged position.

FIG. 24A shows a cross-sectional view from one side of a cup and washer assembly positioned on a driver rod that includes a cover plate. FIG. 24B shows a cross-sectional view from the top of the cup and washer assembly.

FIG. 27A is a side view of an alternate embodiment of an anchor placement device constructed according to the present invention.

FIGS. 27B–27E are cross-sectional views of various embodiments of the shaft of the device of FIG. 27A as taken at A—A.

DETAILED DESCRIPTION

Figure 1A:
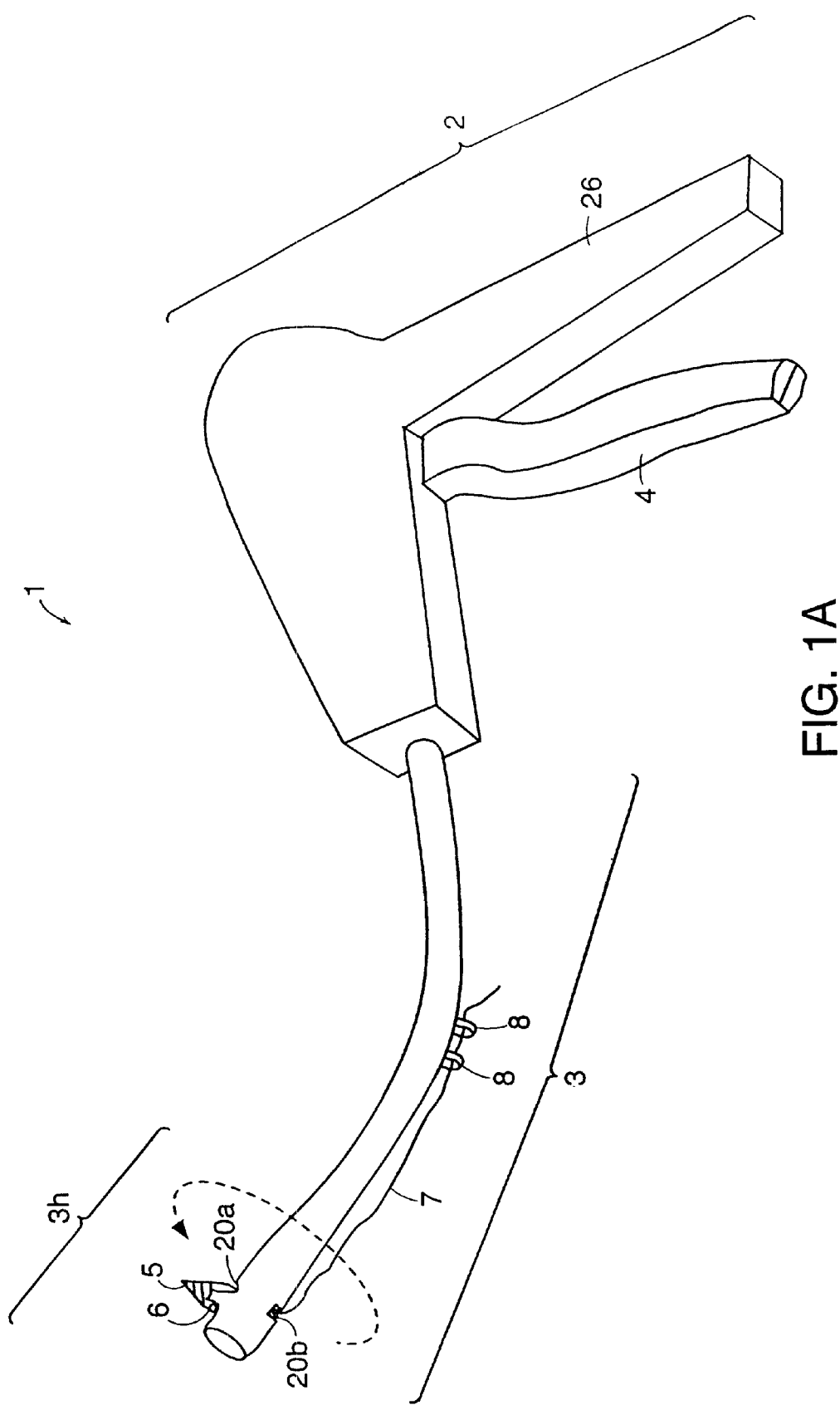
FIG. 1A is a perspective side view of a manual bone anchor placement device within the scope of the present invention.

The manual bone anchor placement devices disclosed provide a mechanism to translate manual linear force (i.e., an operator's hand squeezing a lever) into rotary force on a bone anchor screw. As used herein "placing a bone anchor screw" (or grammatical equivalents thereof) refers to rotational action on, and/or screwing in, of a bone anchor screw into bone. Manual actuation of the disclosed devices occurs when the operator squeezes or pulls a lever with, for example, a single hand. Force on the lever is mechanically transmitted through a force translator to a rotary force mechanism. Each of the disclosed devices is distinguishable by the type of rotary force mechanism used.

In one aspect of the invention, a manual bone anchor placement device uses a rotary force mechanism that includes a resilient element wrapped around a rotator ("wrap-around manual bone anchor placement device"). In a second aspect of the invention, a manual bone anchor placement device ("rack and rotator manual bone anchor placement device") uses a rotary force mechanism that includes a rack and rotator assembly. In a third aspect of the invention, a manual bone anchor placement device uses a rotary force mechanism that includes a cup and washer assembly ("cup and washer manual bone anchor placement device"). A self-tapping bone anchor screw with a preattached suture is also disclosed, which may also be used with any of the aforementioned manual bone anchor placement devices. In addition, a recessed bone anchor mount is disclosed, which may be used with any of the aforementioned manual bone anchor placement devices. All of the devices are useful in, for example, transvaginal bone anchor screw insertion procedures.

Wrap-Around Manual Bone Anchor Placement Device

In the embodiment of the invention shown in FIG. 1, the manual bone anchor placement device 1 is substantially pistol- or gun-shaped. In this embodiment, the manual bone placement device 1 includes a handle 2 and a shaft 3. The handle 2 has a gripping portion 26 to facilitate gripping by the user and a lever 4 through which the user may manually transmit force to the bone anchor placement device 1.

Figure 3A:
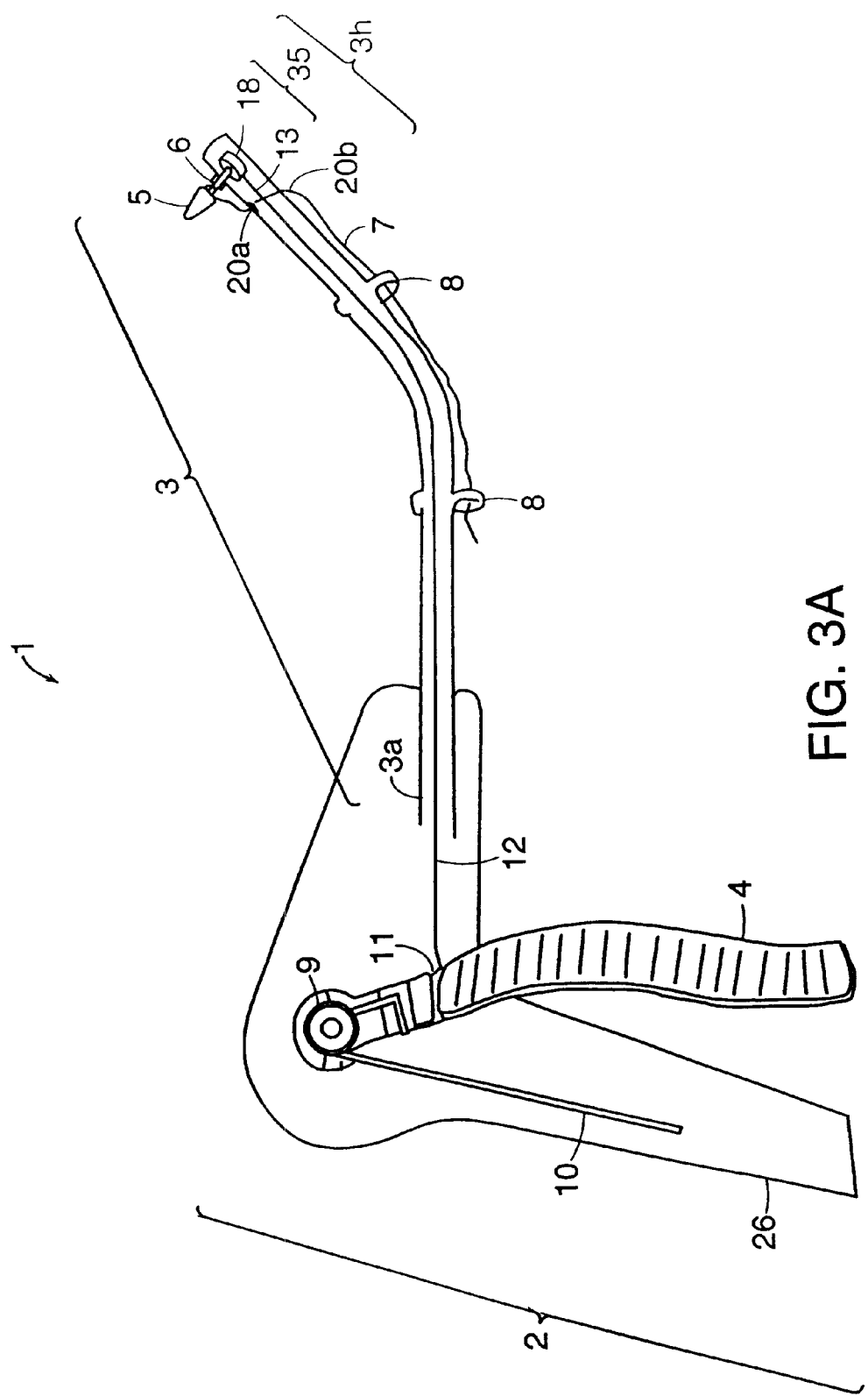
FIG. 3A is a side view of a cross-section through a wrap-around manual bone anchor screw placement device according to one embodiment of the invention showing the components of an action mechanism and a wrap-around rotary force mechanism in which a resilient element is wrapped around a rotator.

As shown in FIG. 3A, the shaft 3 has a first end 3a, proximal to the handle 2, and a second end or head end 3h, distal to the handle 2. A force translator 12 runs through the shaft 2 and transmits linear force exerted manually on the lever 4 to a head assembly 35 positioned at the second end 3h of the shaft 3 (shown enlarged in FIG. 4A). The head assembly 35 is capable of engaging with a bone anchor screw 5 and includes the mechanism that translates linear force from the force translator 12 to rotary force on the bone anchor screw 5.

The shaft 3 is curved to facilitate correct placement of the bone anchor placement device 1 to the proper bone anchor screw insertion site. The shaft 3 is generally linear at its proximal or first end 3a and angles upward near its head end 3h. The upward angle can be from about 0 degrees to about 135 degrees. In one embodiment of the invention, the upward angle is between about 75 degrees and about 100 degrees. In another embodiment of the invention, shown in FIG. 2, the upward angle is approximately 90 degrees. In some embodiments of the invention, the shaft 3 can be rotated about 360 degrees relative to the handle 2 (see dashed arrow in FIG. 1A).

As shown in FIG. 3A, the handle 2 of the manual bone anchor placement device 1 of the present invention may further include an action mechanism through which force from the lever 4 is transmitted to the force translator 12. The action mechanism includes the lever 4, a pivot 9, and the proximal end of the force translator 12. The force translator 12 is connected to the lever 4 by a connector 11 that is positioned beneath the pivot 9. The action mechanism further includes a torsional spring 10 that abuts the lever 4 in the handle 2.

Figure 3B:
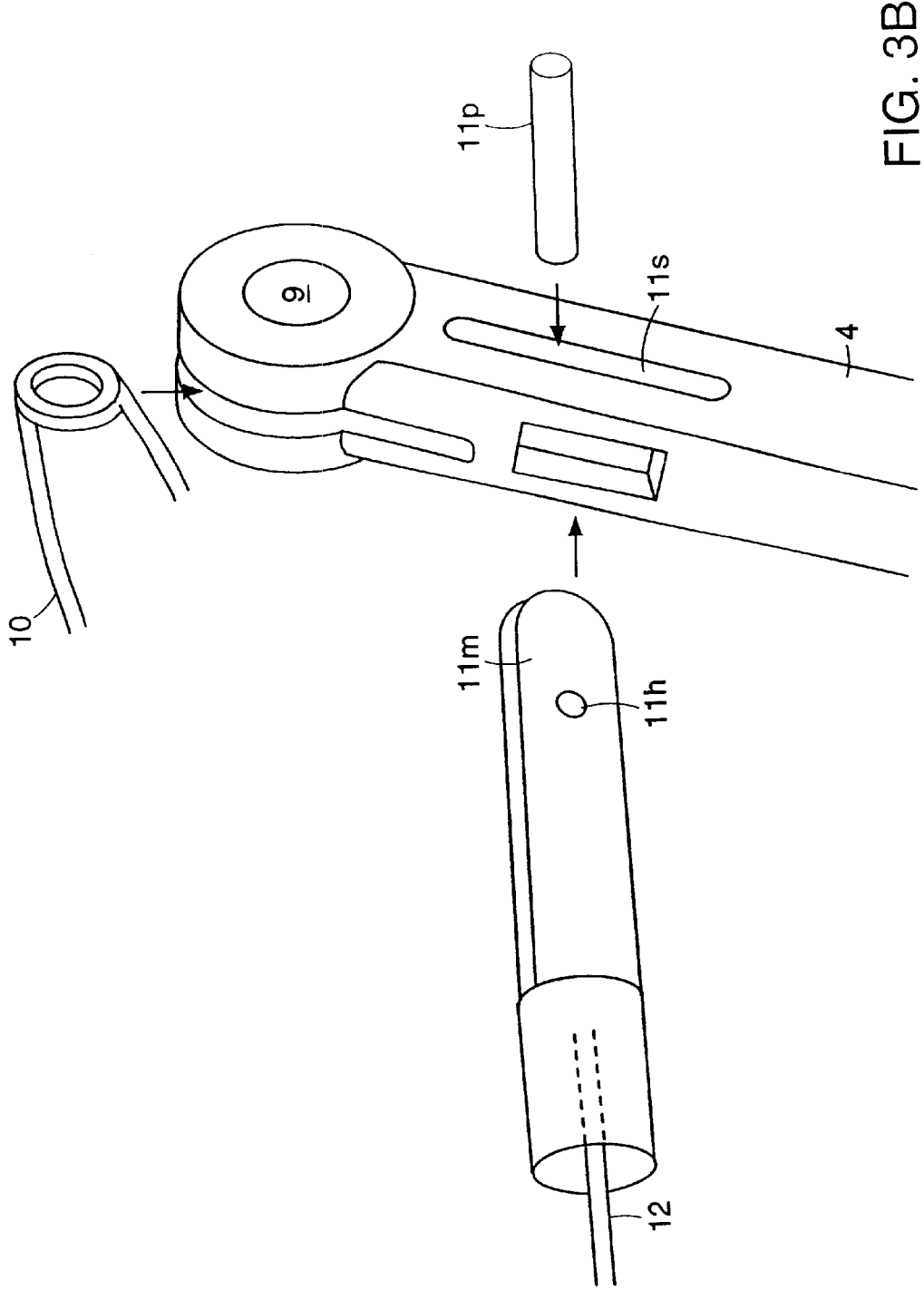
FIG. 3B is an enlarged perspective view of a connector and lever arrangement in an action mechanism according to one embodiment of the invention.

In an embodiment of the invention shown in FIG. 3B, the connector 11 has a "slot and pin arrangement." In this embodiment, a slot 11s is included in the portion of the lever 4 proximal to the pivot 9 and defines openings in the sides, front, and back of the lever 4. A connector member 11m is configured to fit in the slot 11s and includes a pinhole 11h. The connector member 11m is coupled to the force translator 12 at the end of the connector member 11m distal to the pinhole 11h. The connector member is positioned within the slot 11s and secured by a pin 11p that extends through both the slot 11s and the pinhole 11h.

In the embodiment of the invention shown in FIG. 3A, the lever 4 extends at least partially from the handle 2 and linear force on the lever 4 is exerted by pulling on the lever 4. Because the pivot 9 is located above the connector 11, the translator 12 is subjected to tensile loading (e.g., a pulling force) during activation and compressive loading (e.g., a pushing force) during release. The torsional spring 10 abutting the lever 4 thus forces the lever 4 into its original position for the next stroke.

Force exerted on the lever 4 is translated as linear force through the force translator 12. As shown in FIG. 3A, the force translator 12 is a substantially linear member that extends from the handle 2 through the shaft 3 of the manual bone anchor device 1. The force translator 12 may be rigid or flexible, so long as it is tensile. In one embodiment of the invention, the force translator 12 is a wire. Additional types of force translators 12 include, but are not limited to, a cable, a rod, suture material, a string, and the like. Suitable force translator 12 materials include metal, plastic, polymers (e.g., nylon, in the case of suture materials), copolymers, and the like.

In a further embodiment of the invention, washers 21 are positioned on the inside of the shaft 3 to reduce the friction caused by the force translator 12 contacting the inside surfaces of the shaft 3 (see FIG. 4A). The washers 21 can be made of Teflon® material or any material with a low coefficient of friction.

The section of the shaft portion that seats the head assembly 35 may be simply a wider extension of the head end 3h of the shaft 3 shown in FIG. 3A. Alternatively, the head assembly 35 may be provided within a head module 28 seated on the distal-most tip 3b of the shaft (as in FIGS. 4A, 4C, and 4D, for example) and may be either integral with the shaft 3 or separable from the shaft 3. The head assembly 35 includes a rotator 14, a securing element 166, and a resilient element 13, shown in more detail in FIGS. 4A–4D. The resilient element 13 is coupled to both force translator 12 and the rotator 14. In one embodiment of the invention, as shown in FIGS. 4C and 4D, the resilient element 13 is a constant force spring that is welded to the end of the force translator 12 that is proximal to the rotator 14.

Force is transmitted through the resilient element 13 to the rotator 14, which rotates in response to this force. The rotator 14 has at least one protruding portion 15p, shown in more detail in FIGS. 4C and 4D, and is capable of frictionally and mechanically engaging with the securing element 166 (shown in more detail in FIGS. 5A, 5C, 5F, and 5G). The securing element 166 further includes an engaging portion 16 and a mating portion 6. The mating portion 6 of the securing element 166 extends at least partly from the head end 3h of the shaft 3, or the head module 28, and mates with a bone anchor screw 5.

Figure 4C:
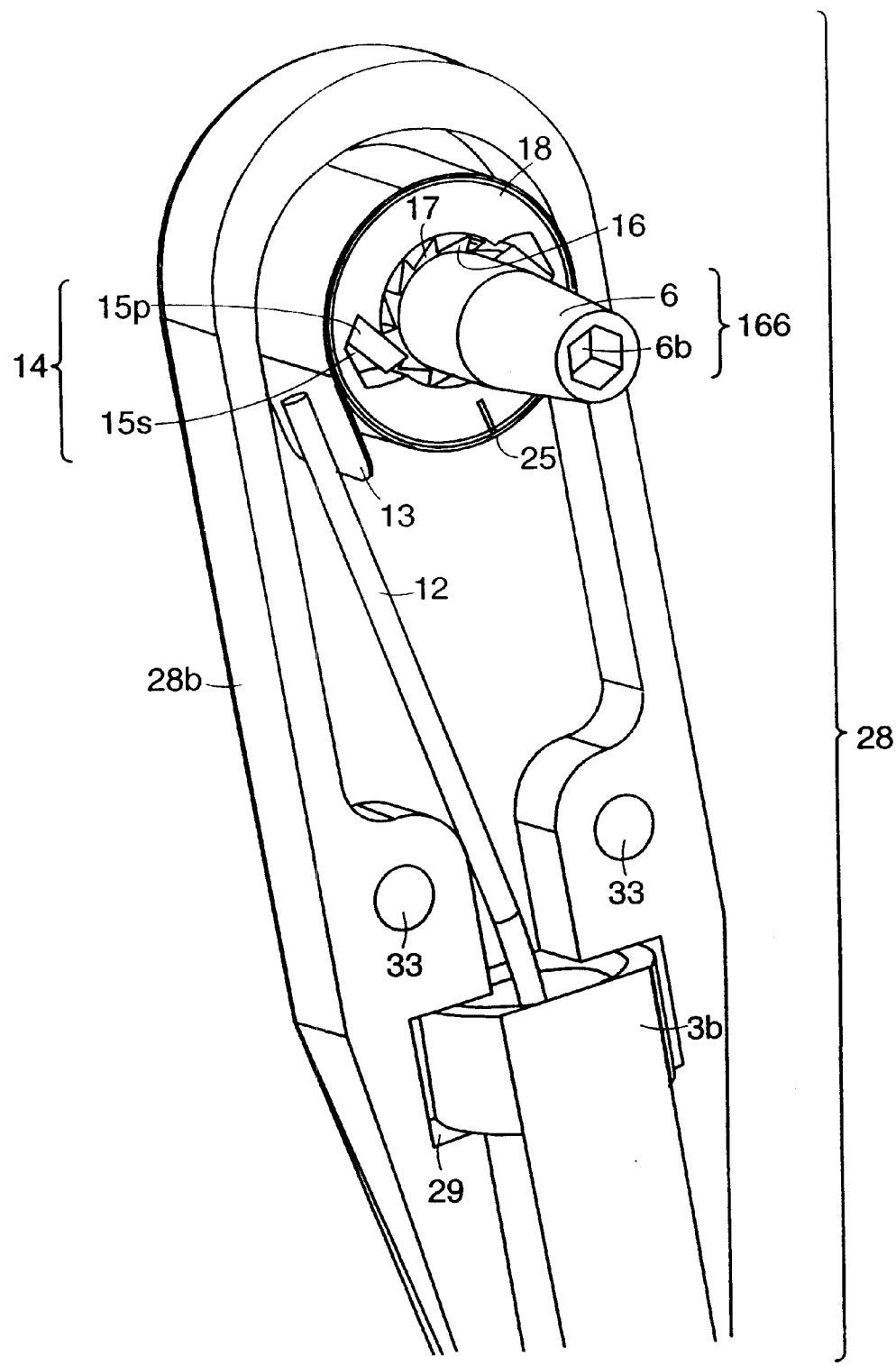
Figure 4D:
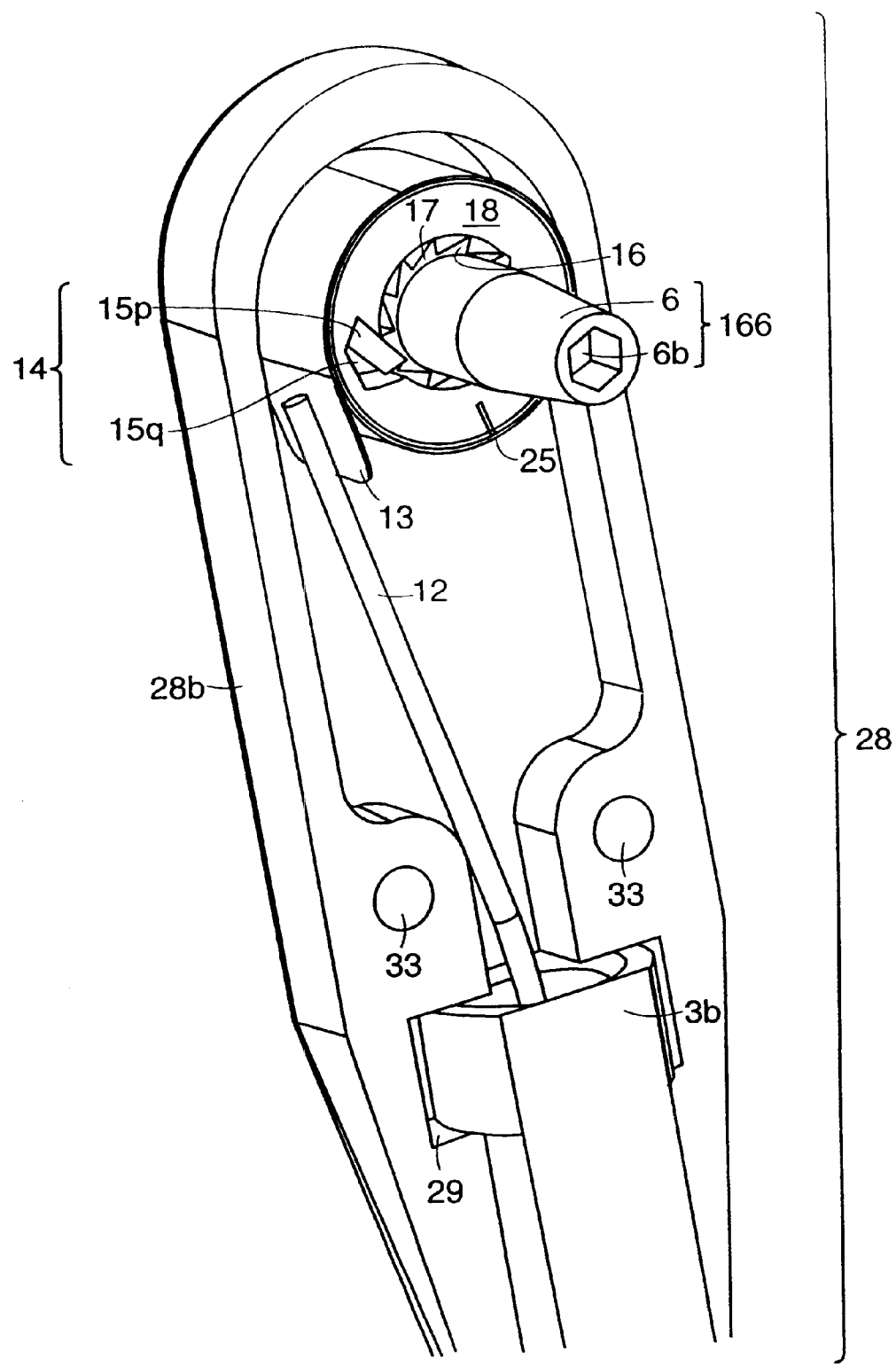
Figure 8A:
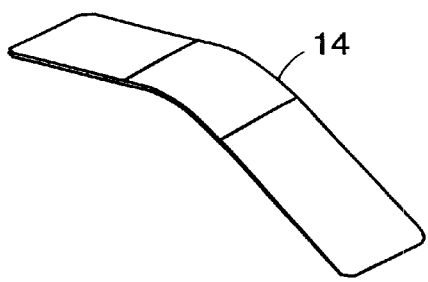
FIGS. 8A–8C show enlarged views of the flat spring portion of a floating pawl used in a wrap-around manual bone anchor placement device.
Figure 8B:
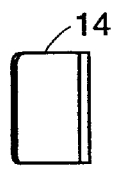
Figure 8C:
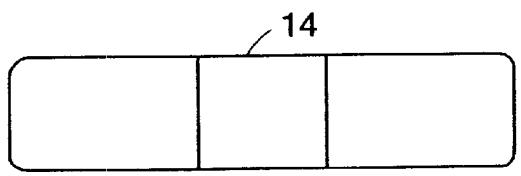

In the embodiment of the invention shown in FIGS. 4A–4C, the rotator 14 has at least one floating pawl and the engaging portion 16 of securing element 166 has teeth 17 that are capable of meshing with the protruding portion 15p of the floating pawl and rotating in response to the rotation of the pawl. The protruding portion 15p extends from a flat spring member 15s as shown in FIGS. 4C and 4D. The flat spring member 15s may be angled or bent, as shown in more detail in FIGS. 8A–8C, to control the position of the protruding portion 15p of the pawl.

It will be readily apparent to one of ordinary skill in the art that any number and type of protruding portions 15p may be provided so long as they are able to frictionally and mechanically engage with the engaging portion 16 of the securing element 166 to cause rotation of the securing element 166. In the embodiment of the invention shown in FIG. 4B, the rotator 14 includes three floating pawls that are spaced equidistant from each other about a central axis of rotation. In another embodiment of the invention, shown in FIG. 4C, the rotator 14 includes two floating pawls, and the teeth 17 of the engaging portion 16 are designed to allow one-directional engagement with the pawls. Slip-free rotation of a bone anchor screw 5 is provided by this design.

Figure 6A:
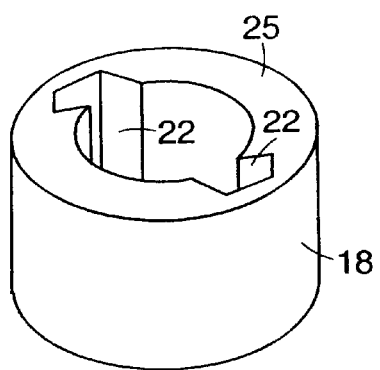
FIGS. 6A–6C show enlarged views of the rotatable housing used in a wrap-around manual bone anchor placement device.
Figure 6B:
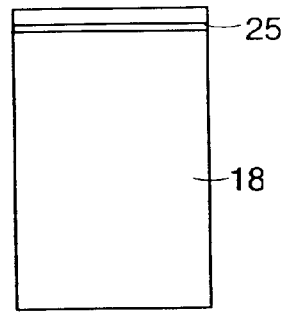
Figure 6C:
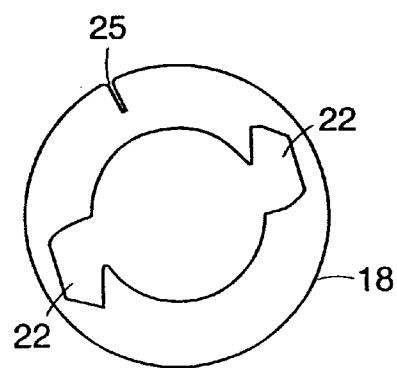
Figure 7A:
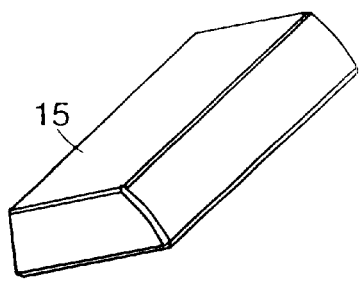
FIGS. 7A–7C show enlarged views of the floating portion of a floating pawl used in a wrap-around manual bone anchor placement device.
Figure 7B:
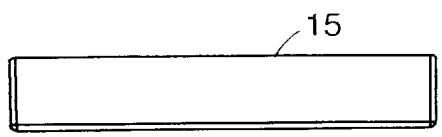
Figure 7C:
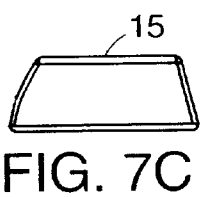

In the embodiment of the invention shown in FIGS. 4C and 4D, the rotator 14 is contained within a rotatable housing 18 positioned within the head module 28 and is fitted into at least one groove 22 within the inner wall of the rotatable housing 18. FIGS. 6A–6C show enlarged views of the rotatable housing 18. In the embodiment of the invention shown in FIGS. 6A and 6C, the rotatable housing 18 has two grooves 22 to accommodate a rotator 14 that includes two floating pawls.

Figure 9:
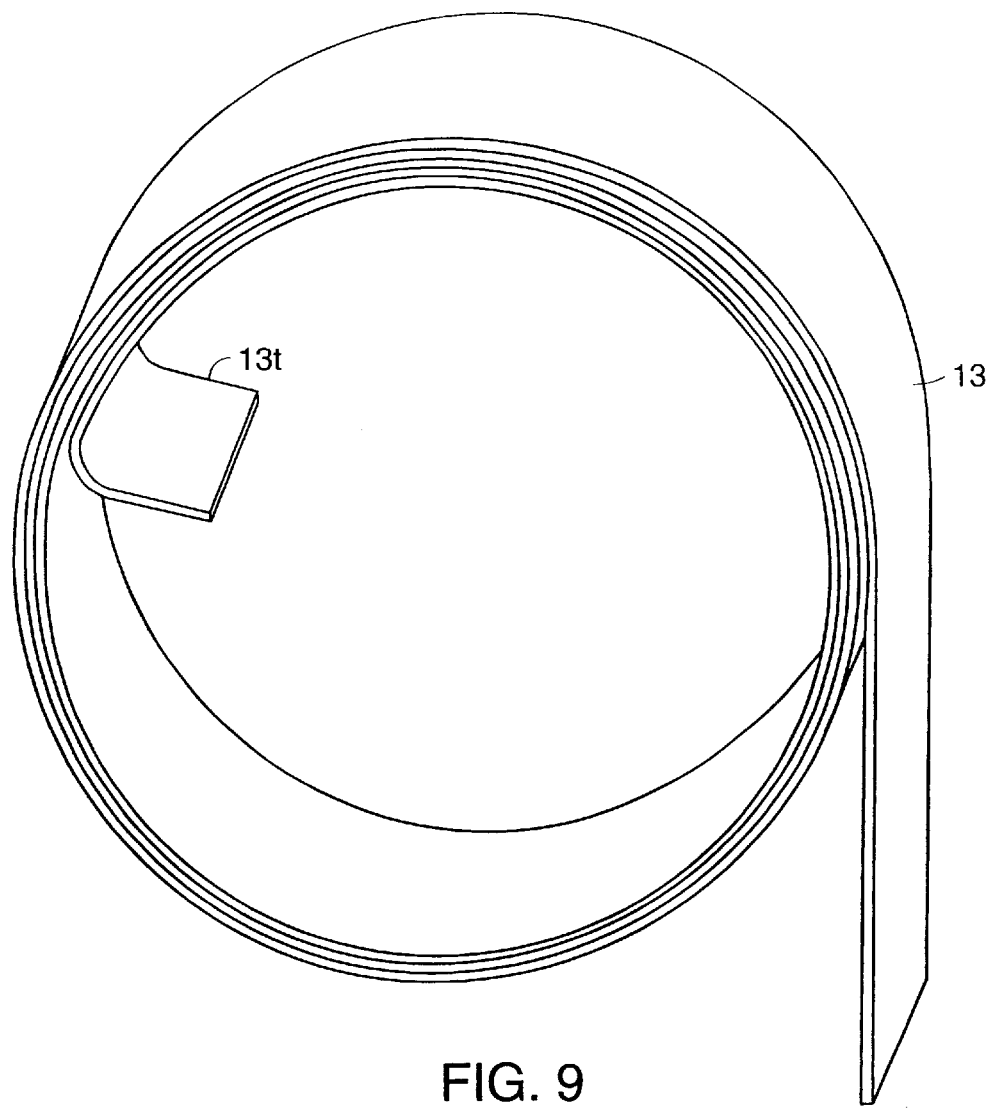
FIG. 9 shows an enlarged view of a resilient element used in a wrap-around manual bone anchor screw placement device.

In the embodiment of the invention shown in FIGS. 4A–4D, the resilient element 13 is at least partially wound around the rotatable housing 18, and the rotatable housing 18 and the rotator 14 move as one. The resilient element 13 is secured to the rotatable housing 18 by the insertion of an inwardly projecting tail 13t of the resilient element 13 into a notch 25 in the rotatable housing 18. An enlarged view of the resilient element 13 and inwardly projecting tail 13t is shown in FIG. 9.

Figure 10:
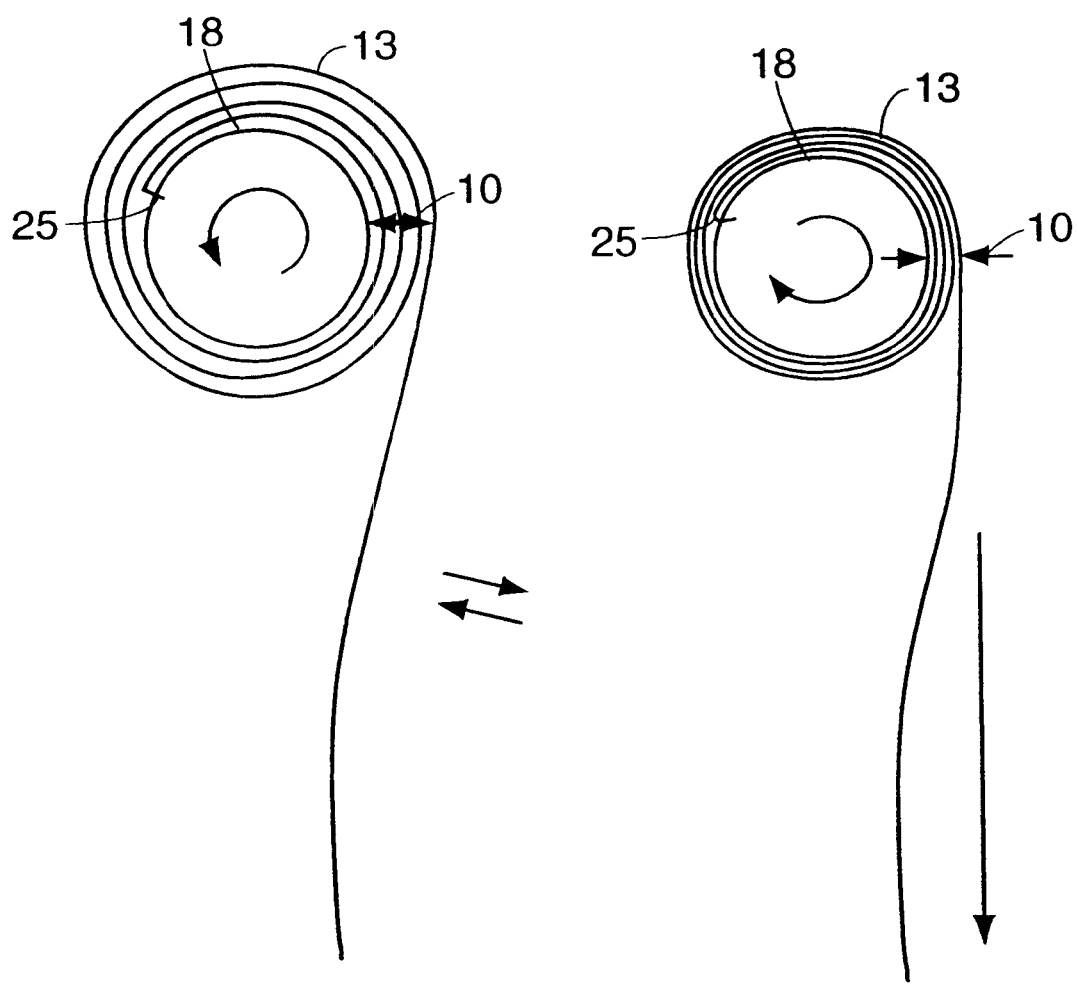
FIG. 10 shows a schematic view of how force is transmitted through the resilient element in a wrap-around manual bone anchor placement device.

As shown schematically in FIG. 10, force transmitted through the resilient element 13 causes the inner diameter ID of the resilient element 13, which is wrapped around the rotatable housing 18, to decrease and the resilient element 13 to grip the rotatable housing 18, resulting in its rotation. Upon elimination of force on the resilient element 13, the inner diameter ID of the portion of the resilient element 13 wrapped around the rotatable housing 18 gets larger, resulting in free rotation in the opposite direction. The gripping action in one direction and the slipping action in the opposite direction provide the action needed to drive a bone anchor screw 5 into the bone when a linear pull force is exerted on the lever 4.

In the embodiment of the invention shown in FIGS. 4C and 4D, the securing element 166 is positioned at least partially within the rotatable housing 18, and the engaging portion 16 of the securing element 166 rotates in response to the rotation of the rotatable housing 18 and rotator 14.

Figure 5A:
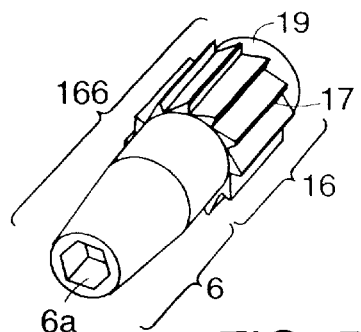
FIGS. 5A–5H show enlarged views of securing elements used with a wrap-around manual bone anchor placement device and bone anchor screws according to different embodiments of the invention.
Figure 5B:
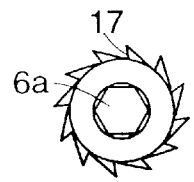
Figure 5C:
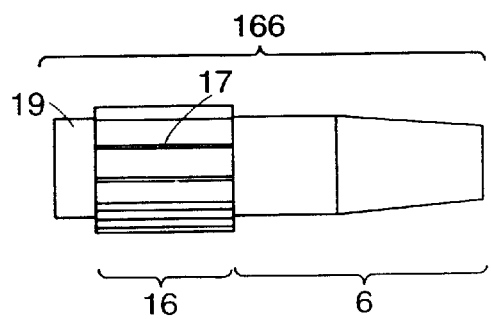
Figure 12D:
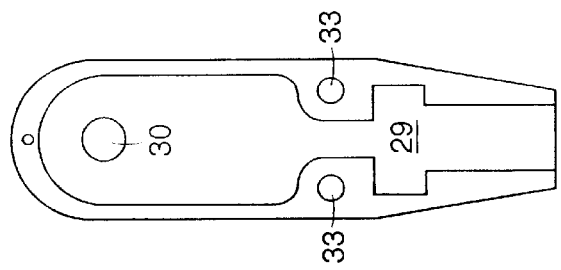
FIGS. 12A–12I show enlarged views of a head module of a wrap-around manual bone anchor placement device according to one embodiment of the invention.
Figure 12C:
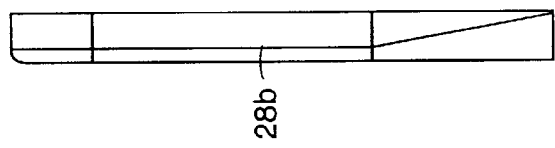
Figure 12A:
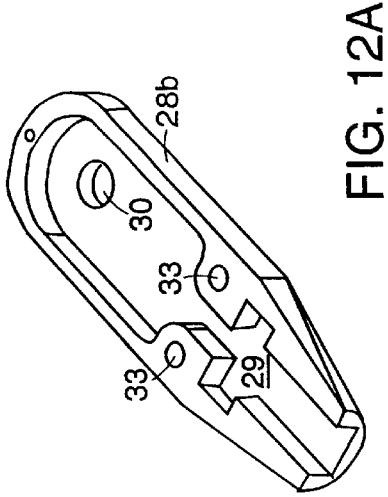
Figure 12B:
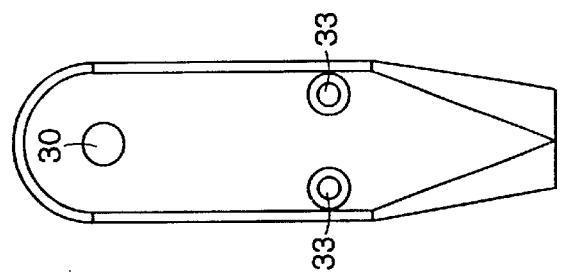
Figure 12I:
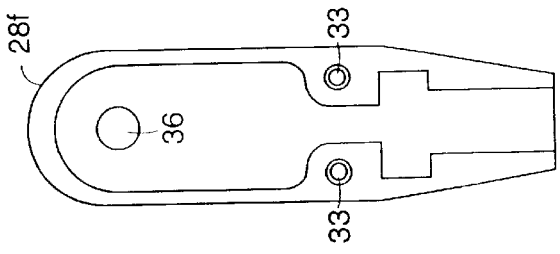
Figure 12F:
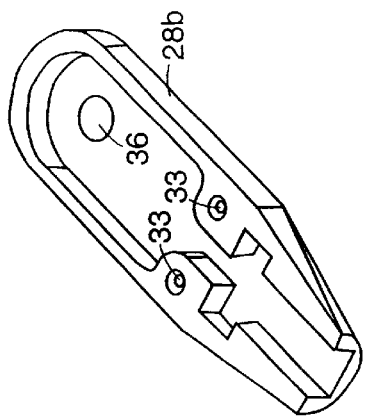

As shown in the enlarged view of the securing element 166 provided in FIGS. 5A and 5C, the securing element 166 further includes a generally cylindrical front piece 19 that extends from the engaging portion 16 of the securing element and fits into a complementary recessed portion 30 in the inner wall of the head end 3h of the shaft 3 or the head module 28 (shown in FIGS. 12A, 12B, and 12C). The front piece 19 acts to position the rotatable housing 18 within the head end 3h of the shaft 3 or within the head module 28 (as shown in FIGS. 12A, 12B, and 12C), allowing it to rotate freely about the axis defined by the front piece 19.

Figure 5D:
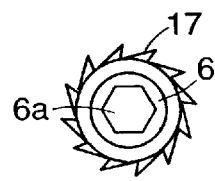

The mating portion 6 of the securing element 166 extends at least partially outside the head end 3h of the shaft 3. The bone anchor screw 5 may be seated on the mating portion 6 of the securing element 166 in a variety of ways and the mating portion 6 of the securing element 166 may be fabricated to complement a variety of different types of bone anchor screws 5. In one embodiment of the invention, shown in FIG. 5E, when the bone anchor screw 5 being used provides a shaft 5a with a hex-shape, the mating portion 6 of the securing element 166 is designed to provide a recess 6a that has a hex-shaped cross-section (see FIGS. 5A, 5B, and 5D). It will be readily apparent to one of ordinary skill in the art that the recess 6a of the mating portion 6 of the securing element 166 may be any type of shape (e.g., a T-shape or an X-shape) that allows for frictional and mechanical engagement with a bone anchor screw 5 having a shaft 5a with the corresponding shape. In a further embodiment of the invention, shown in FIGS. 5F and 5G, the mating portion 6 of the securing element 166 has a shaft 6b while the bone anchor screw 5 (shown in FIG. 5H) provides a recess 5b complementary to the shape of the shaft 6b Any type of bone anchor screw 5 may be used adaptable to the mating portion 6 of a selected securing element 166. In one embodiment, shown in FIG. 1A, the bone anchor screw 5 has a pre-attached suture 7 and the walls of the shaft 3 defining the head end 3h of the shaft have aligned openings 20a and 20b through which the suture 7 is threaded. (Aligned openings may also be provided in the head module 28 in embodiments of the invention where the bone anchor placement device comprises a head module 28.) Attachment of the suture 7 along the length of the shaft 3 will keep the suture 7 from becoming entangled during the bone anchor screw insertion procedure.

Figure 1B:
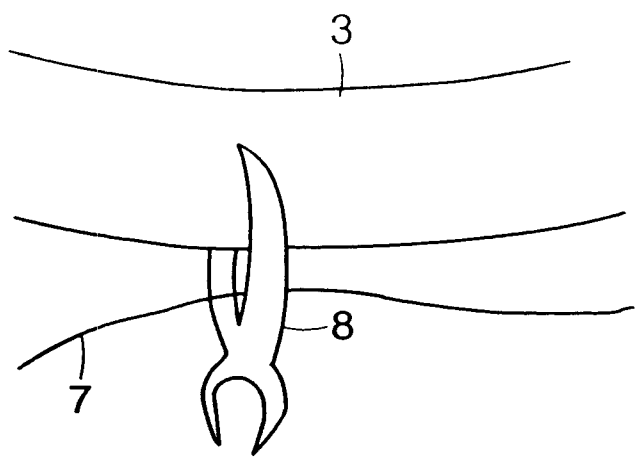
FIG. 1B shows a section of a side-view of the shaft of a manual anchor placement device to which a suture ring is clipped and through which a suture is threaded.
Figure 1C:
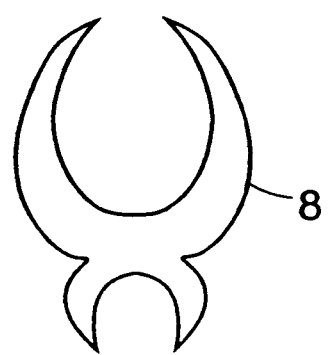
FIG. 1C shows an enlarged cross-sectional view of a suture ring.

In the embodiment of the invention shown in FIGS. 1A–1C, the length of the suture 7 extending out of the head end 3h of the shaft 3 may be secured by one or more suture rings 8 mounted on the shaft 3. The suture rings 8 may be an integral part of the shaft 3 or may be clipped on as shown in FIG. 1B. After the bone anchor screw 5 is seated, the bone anchor screw 5 disengages from the mating portion 6 of the securing element 166. The suture 7 then slips through aligned openings 20a and 20b at the head end 3h of the shaft 3 and through the suture rings 8, disengaging from the bone anchor placement device 1.

Figure 2:
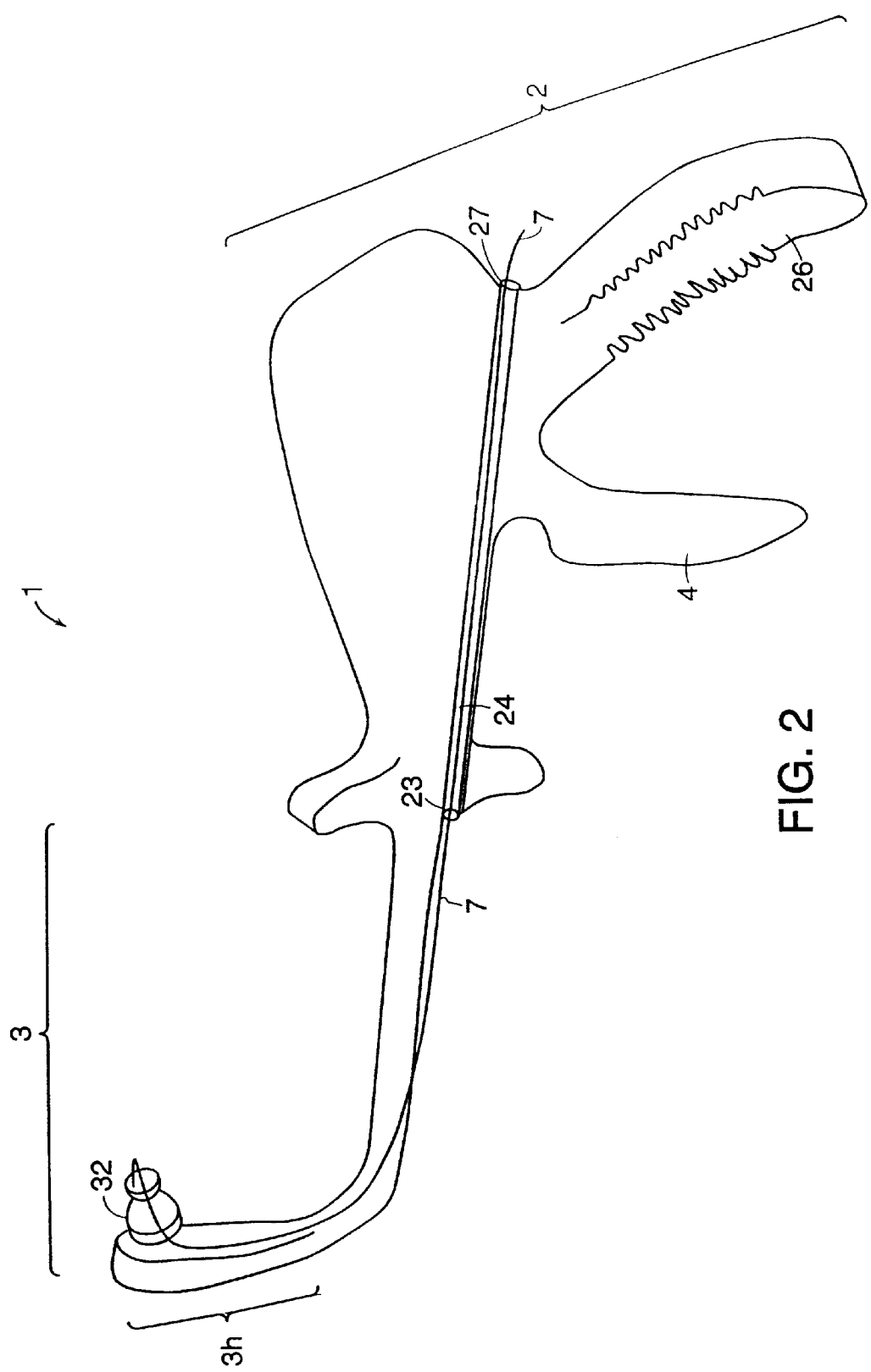
FIG. 2 shows a perspective side view of a manual bone anchor placement device according to one embodiment of the present invention. In this embodiment, the manual bone anchor placement device comprises a groove cut into the outer surface of the handle through which a suture is threaded and the shaft of the manual bone anchor placement is angled upwards at about a 90-degree angle.

In another embodiment of the invention, shown in FIG. 2, a groove 23 is cut into the outer surface of the handle 2, extending in a line parallel to the longitudinal axis of the shaft 3, which is proximal to the gripping portion 26 of the handle 2. In this embodiment of the invention, the suture 7 is enclosed within a flexible, molded sleeve 24, composed of Teflon® material, for example, which is press-fitted into the groove 23 of the handle 2. In a further embodiment of the invention, a retaining clip 27 may be provided at the end of the sleeve 24 proximal to the gripping portion 26 of the handle 2 to prevent the suture 7 from slipping out before the bone anchor screw 5 is screwed into the bone. The user of the manual bone anchor placement device 1 may then cut the retaining clip 27, which allows the suture 7 to slide out of sleeve 24 after the bone anchor 5 is screwed into the bone.

In further embodiments of the invention, the manual bone anchor placement device 1 may be fabricated from modules including a handle module and a shaft module, allowing the user to mix and match different handles 2 with different shafts 3 (including different head assemblies 35). In the embodiment of the invention shown in FIG. 11, the handle module comprises the two halves 2a and 2b of the handle 2 (including the two halves 26a and 26b of the gripping portion 26) that are separable from each other. In this embodiment, an old shaft 3o may be removed from the handle 2 upon disconnecting the force translator 12 from the connector 11. A new shaft 3nu may then be positioned within the handle 2. After connecting the force translator 12 of the new shaft 3nu to the connector 11, the two halves 2a and 2b of the handle 2 are snapped back together and the wrap-around manual bone anchor placement device 1 is ready for use.

Figure 11:
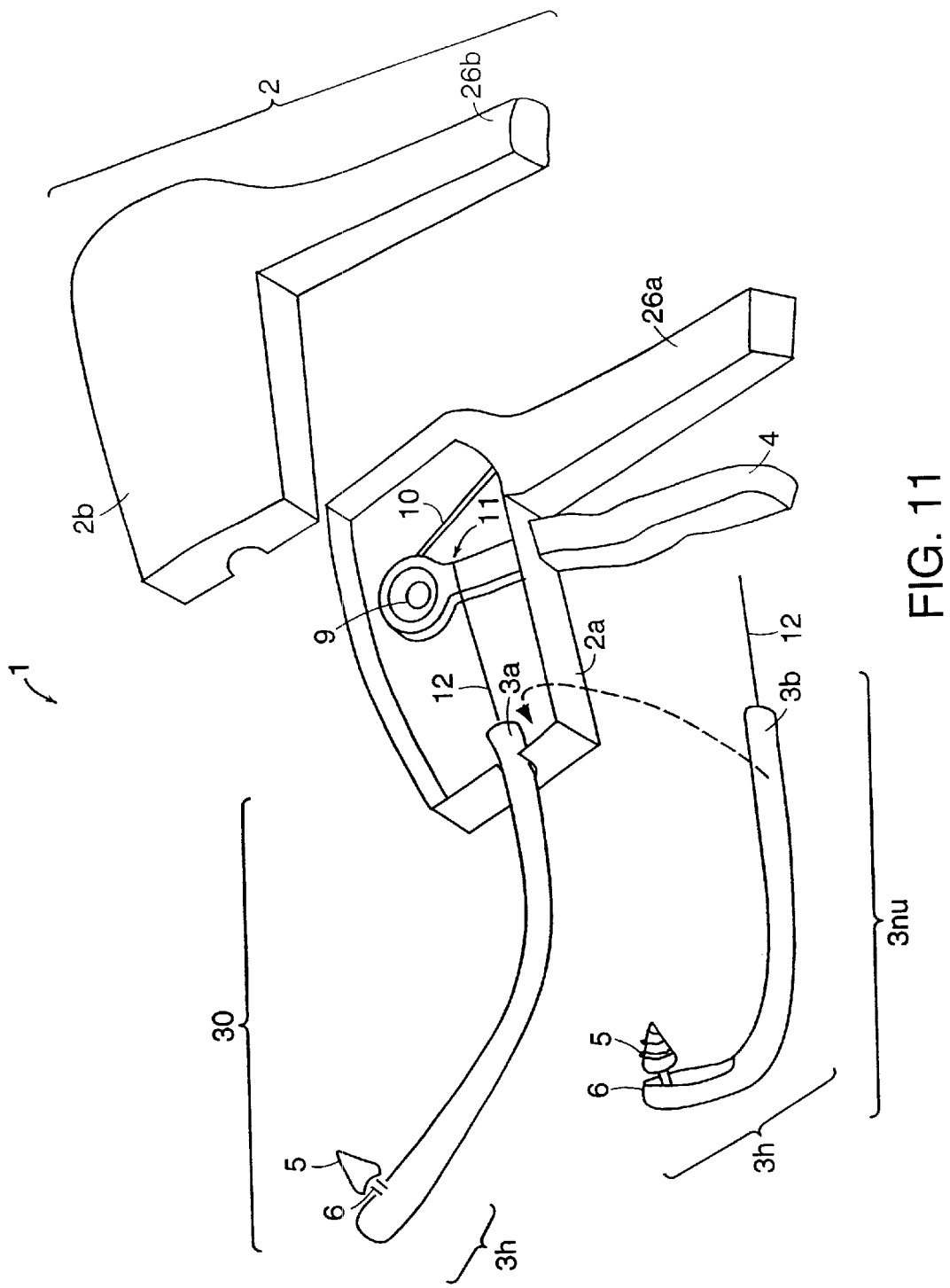
FIG. 11 shows a perspective view of a wrap-around manual anchor placement device according to one embodiment of the invention where the shaft and handle portions include interchangeable modules.

In the embodiment shown in FIG. 11, interchanging the old shaft 3o from the original bone anchor placement device 1 with a new shaft 3nu provides the user with the opportunity to replace a shaft 3 with an approximately 30 degree upward angle with one with an approximately 90 degree upward angle and a different type of head end 3h. The modular nature of the wrap-around bone anchor placement device 1 thus allows users to select the type of shaft 3 or head end 3h/head module 28/head assembly 35 that best suits their needs and facilitates repairs of the device 1.

As shown in FIGS. 12A–12I, the front half 28f and back half 28b of the head module 28 may also be separated by unscrewing screws at coupling regions 33. This allows the user to vary the exact configuration of the head module 28 and head assembly 35 being used with a particular shaft 3.

Figure 12H:
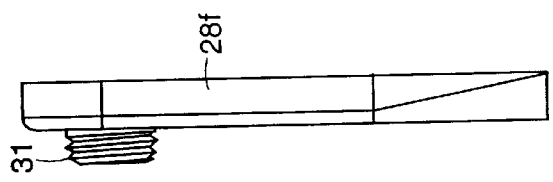
Figure 12E:
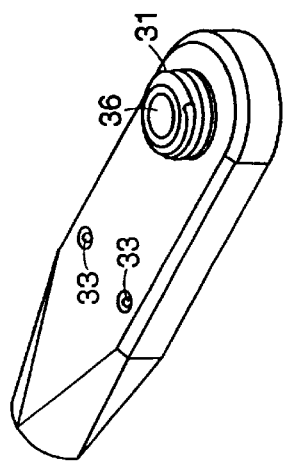
Figure 12G:
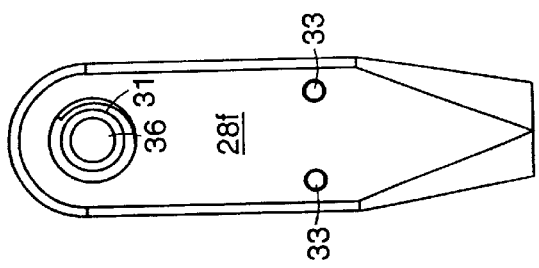
Figure 13A:
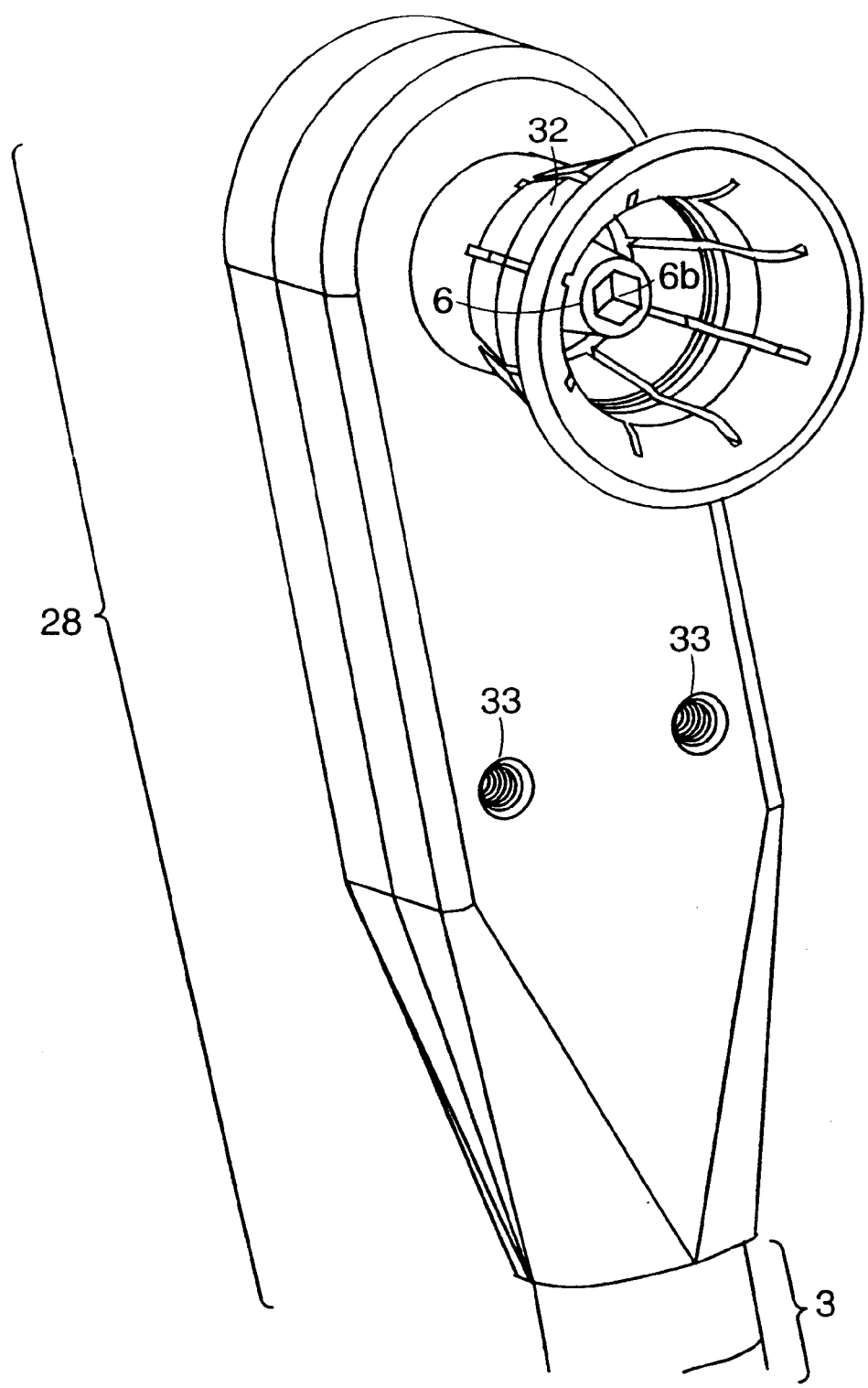
FIG. 13A shows an enlarged perspective view of a head module of a wrap-around manual bone anchor placement device according to one embodiment of the invention where a protective sheath is provided to protect the bone anchor screw and the portion of the securing element that protrudes from the head module.
Figure 13B:
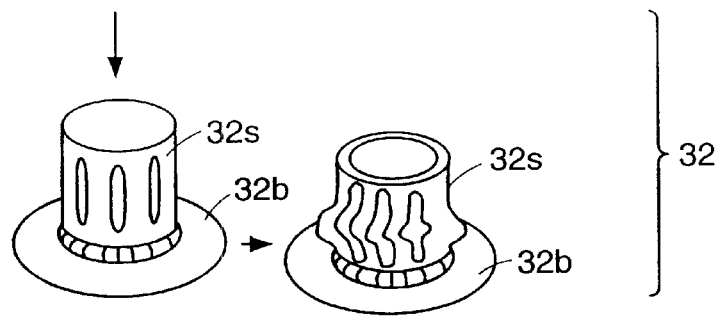
FIG. 13B shows an enlarged perspective view of a collapsible protective cover for a bone anchor screw. The left-hand side of the Figure shows the cover in an uncollapsed state. The right-hand side of the Figure shows the cover in a collapsed state.
Figure 13C:
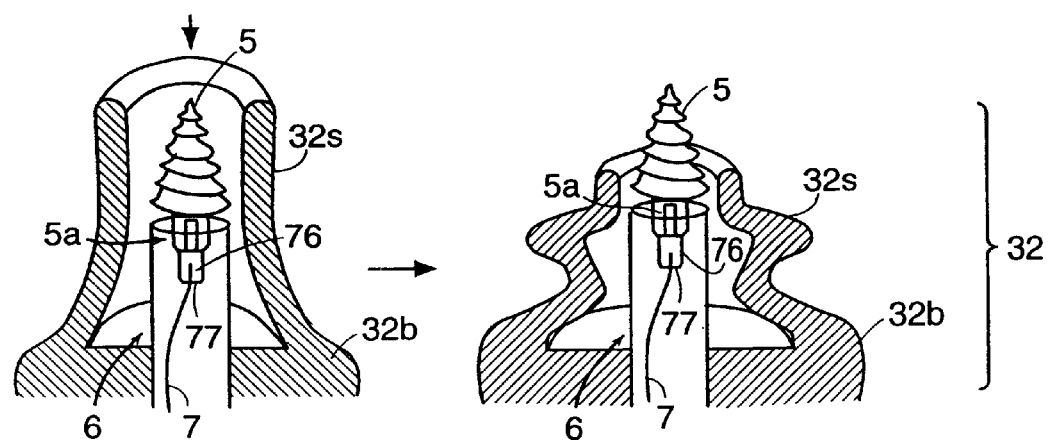
FIG. 13C shows an enlarged cross-sectional view of a collapsible protective cover surrounding a bone anchor screw. The left-hand side of the Figure shows the cover in an uncollapsed state and completely surrounding a bone anchor screw. The right-hand side of the Figure shows the cover in a collapsed state, exposing the bone anchor screw.

In the embodiment shown in FIGS. 12E, 12G, and 12H, the front half of the head module 28f may also be provided with a protruding threaded element 31. As shown in FIG. 13A, a protective cover 32 may be seated on this threaded element 31, providing a covering for the bone anchor screw 5 extending outside of the head module through opening 36 and protecting the tip of the bone anchor screw 5 from damage before it contacts a bone insertion site. In a further embodiment of the invention, shown in FIGS. 13B and 13C, the protective cover for protecting a bone anchor screw has a base 32b for engaging the shaft 3 of the manual bone anchor placement device 1, and a sheath 32s coupled to the base 32b for surrounding and protecting the bone anchor screw 5. The sheath 32s is collapsible and collapses as the bone anchor screw 5 is driven into bone, thereby uncovering the bone anchor screw 5. Sheath 32s materials include flexible plastic, rubber, thin pleated metal, and the like.

Figure 14:
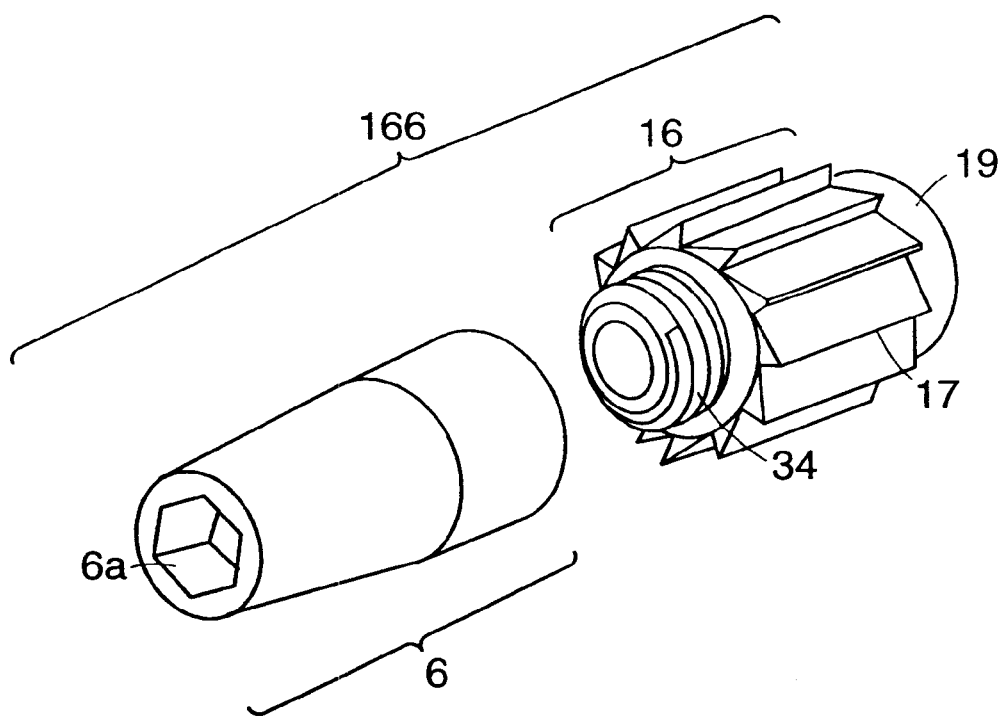
FIG. 14 shows an enlarged version of a securing element used in a wrap-around manual bone anchor placement device according to one embodiment of the invention where the mating portion of the securing element may be uncoupled from the engaging portion of the securing element.

In still a further embodiment of the invention, shown in FIG. 14, the mating portion 6 of the securing element 166 may be uncoupled from the engaging portion 16 of the securing element 166 without opening the head end 3h or head module 28. In this embodiment of the invention, the mating portion 6 of the securing element 166 is threaded onto a threaded element 34 that protrudes from the engaging portion 16 of the securing element 166 and may be unscrewed from the engaging portion 16 of the securing element 166. This embodiment of the invention allows different types of mating portions 6 to be coupled to the engaging portion 16 of the securing element 166 and thus allows the user to select a mating portion 6 of a securing element 166 that is complementary to any desired type of bone anchor screw 5.

Rack and Rotator Manual Bone Anchor Placement Device

Figure 15:
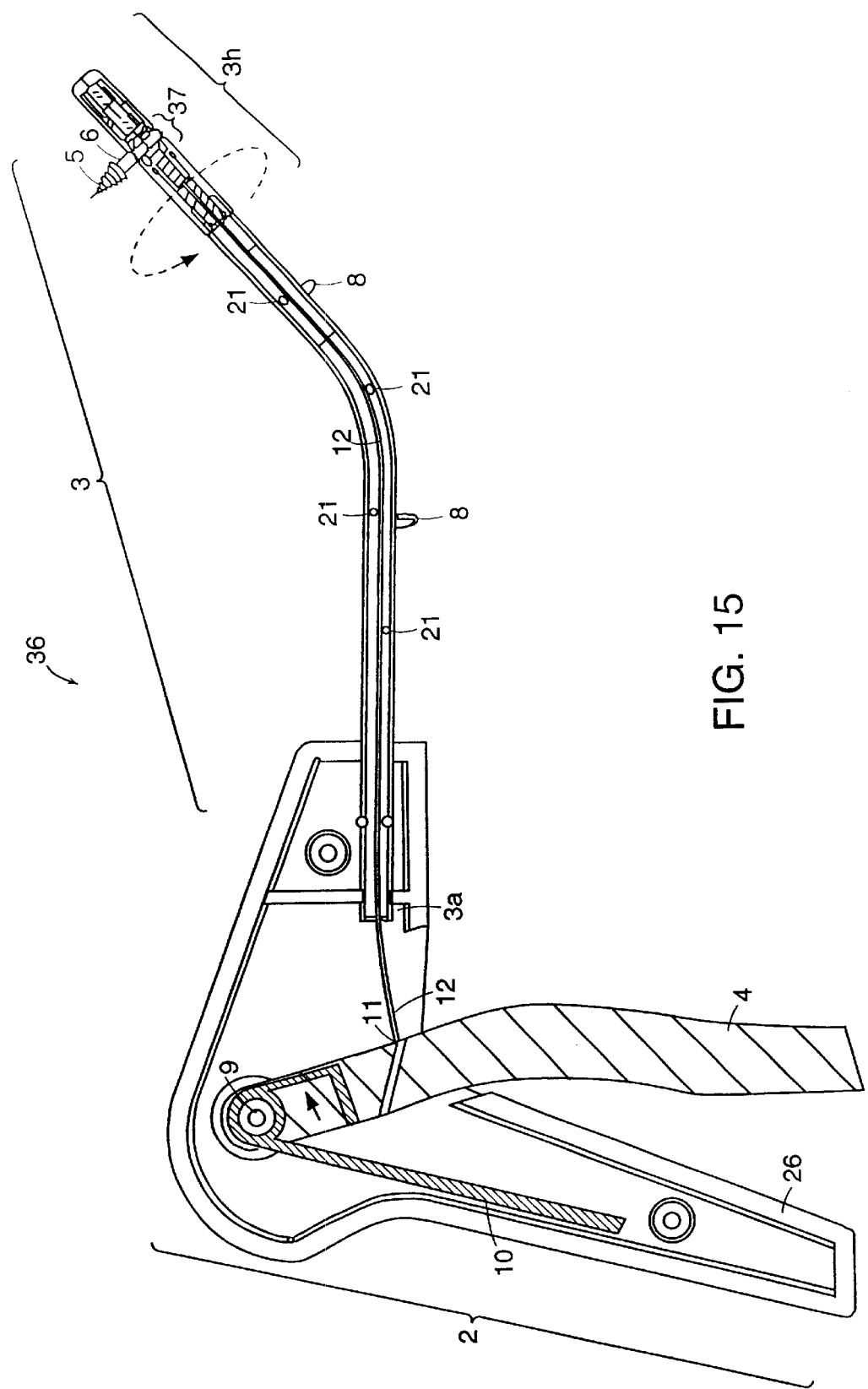
FIG. 15 is a side view of a cross-section through a rack and rotator manual bone anchor placement device according to one embodiment of the invention, showing the components of an action mechanism and a rack and rotator rotary force mechanism.

As shown in FIG. 15, the rack and rotator manual bone anchor placement device 36, like the wrap-around device 1, is substantially pistol- or gun-shaped and includes a handle 2 and a shaft 3. The handle 2 includes a gripping portion 26 and a lever 4 through which a user may manually transmit linear force to the rotary force mechanism of the device 36. Like the wrap-around device 1, the shaft 3 of the rack and rotator manual bone anchor placement device 36 has a first end 3a proximal to the handle 2, and a second end, or head end 3h, distal to the handle 2.

As in the wrap-around device 1, the shaft 3 of the rack and rotator manual bone anchor placement device 36 is curved to facilitate correct placement of the bone anchor placement device 36 to the proper bone anchor screw insertion site, angling upward near its head end 3h. The upward angle can be from about 0 degrees to about 90 degrees. In one embodiment of the invention, the upward angle is between about 35 degrees and about 60 degrees. In the embodiment of the invention shown in FIG. 15, the upward angle is approximately 45 degrees. The upward angle of the shaft 3 may be optimized to facilitate insertion of a bone anchor screw 5. The shaft 3 can also be rotated about 360 degrees relative to the handle portion 2 (see dashed arrow in FIG. 15).

As in the wrap-around manual bone anchor placement device 1, the rack and rotator manual bone anchor placement device 36 has an action mechanism through which force on the lever 4 is transmitted to the force translator 12. The action mechanism includes lever 4, pivot 9, and the proximal end of the force translator 12. A torsional spring 10 abuts the lever 4 in the handle 2. The force translator 12 is connected to the lever 4 by a connector 11, but the position of the connector 11 relative to the pivot 9 may be varied. As in the wrap-around manual bone anchor device 1, the force translator 12 may be rigid (e.g., a rod) or flexible (e.g., a spring, wire, string, suture material, or the like).

Unlike the wrap-around bone anchor placement device 1, in which a pushing force is transmitted to the force translator 12 by squeezing the lever 4 towards the gripping portion 26 of the handle 2, the rack and rotator bone anchor placement device 36 may be configured so that either a push force or a pull force may be transmitted through the force translator 12 by squeezing the lever 4.

In the "pull" embodiment, shown in FIG. 18A, pivot 9 is positioned above connector 11. In this embodiment, mechanical actuation of the lever 4 causes the force translator 12 to be subjected to tensile loading, i.e., a pulling force, when the user squeezes the lever 4 toward the gripping portion 26 of the handle 2, and compressive loading when the user releases the lever 4.

Figure 18B:
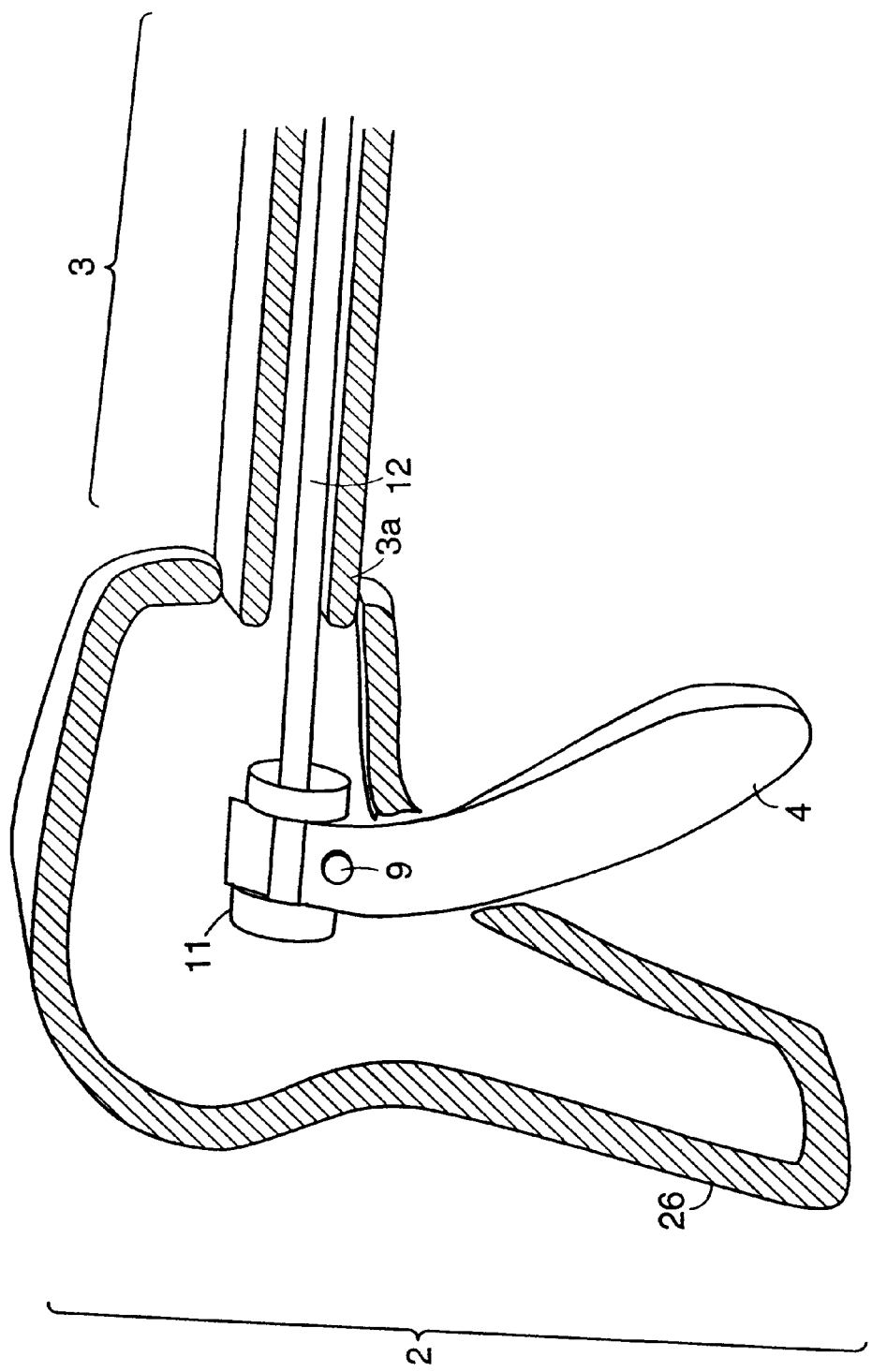

In the "push" embodiment shown in FIG. 18B, pivot 9 is positioned below connector 11 which connects force translator 12 to the lever 4. Squeezing the lever 4 in this embodiment causes the force translator 12 to be subjected to compressive loading, or a pushing force.

Force translator 12 runs through the shaft 3 and transmits linear force exerted manually on the lever 4 to a head assembly 37 positioned at the head end 3h of the shaft 3. Washers 21 positioned on the inside of the shaft 3 reduce the friction caused by the force translator 12 contacting the inside surfaces of the shaft 3 (see FIG. 15).

Head assembly 37 includes a rack 38 and a rotator 14. The rotator 14 includes at least one protruding portion 15p, and a coupler 43. Head assembly 37 performs a similar function in the rack and rotator bone anchor placement device 36 as head assembly 35 does in the wrap-around device 1, translating linear force from the force translator 12 to rotary force on a bone anchor screw 5, but does so through a different mechanism.

Figure 16:
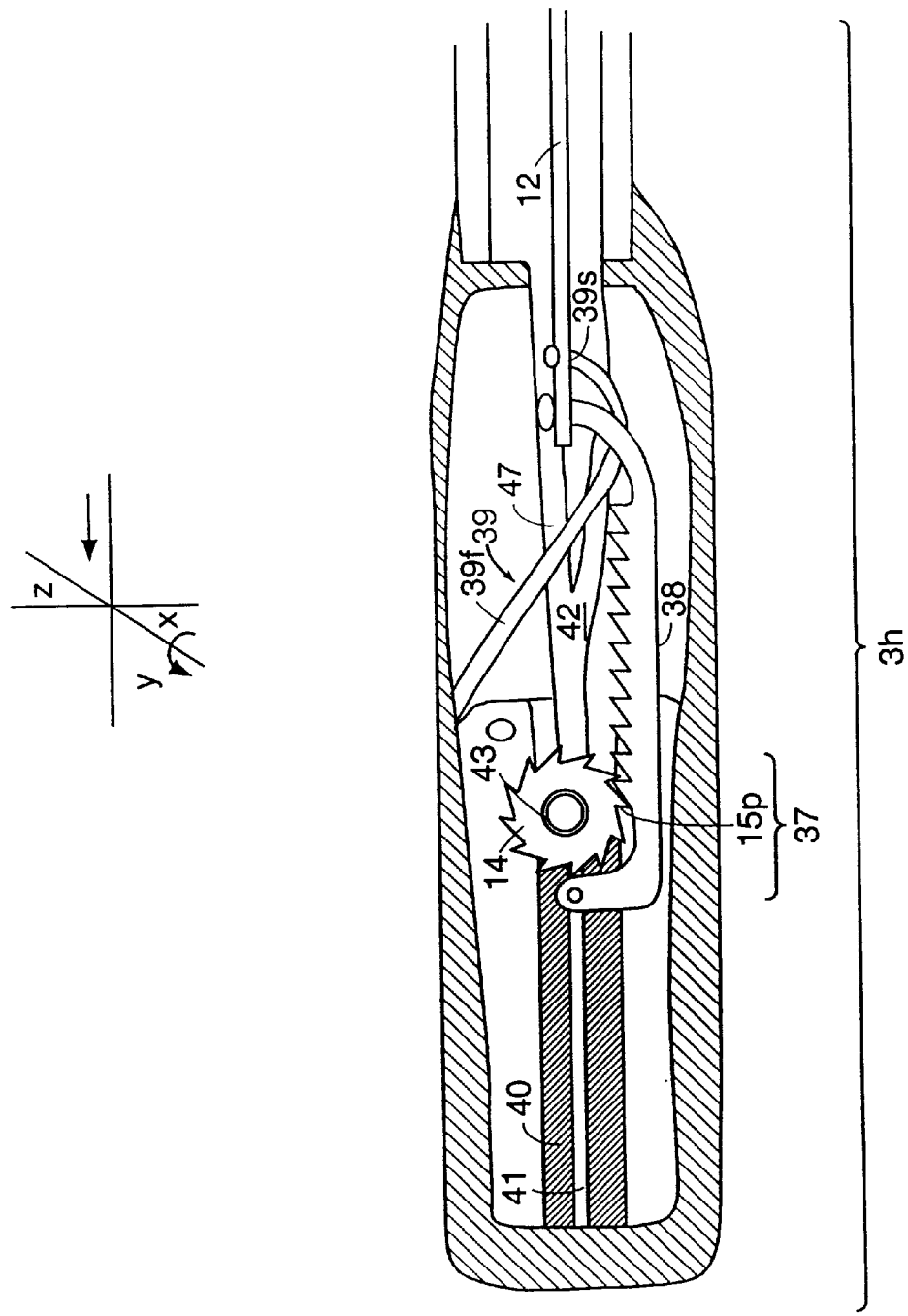
FIG. 16 shows an enlarged view of a head assembly in a rack and rotator manual bone anchor screw placement device in which the rotator comprises a ratchet wheel.

As shown in FIG. 16, the distal end of the force translator 12 is coupled to rack 38, which is positioned proximal to rotator 14. The rack 38 is only able to move in the y direction while the rotator 14 is only able to move rotationally about the x-axis. When the rack 38 moves into an engaging position relative to the rotator 14, the teeth of rack 38 mesh with the protruding portion 15p of rotator 14, causing the rotator 14 to rotate. Thus, linear force transmitted through the force translator 12 translates into movement of the rack 38 along the y-axis, which in turn translates into rotation of the rotator 14 about the x-axis. The rotator 14 is coupled to coupler 43, which is capable of mating with or engaging a bone anchor screw 5. Rotation of the rotator 14 is translated into a torque applied on the coupler 43, which in turn drives or screws a bone anchor screw 5 into bone. Rotators 14 that may be used with racks 38 of the present invention include ratchet wheels, pawls, pinions, gears, and the like.

In the embodiment of the invention shown in FIG. 16, the rotator 14 is a ratchet wheel. In this embodiment of the invention, the interior of the head end 3h of the shaft 3 comprises a grooved element 40 that includes an actuating groove 41 and a return groove 42. A head assembly spring 39 is also positioned within the head end 3h and is coupled by a first end 39f to the inner wall of the head end 3h of the shaft 3 distal to rack 38 and at a second end 39s to force translator 12. Squeezing lever 4 exerts a linear pull force on the translator 12, which mechanically pulls the rack 38 along the actuating groove 41 towards the rotator/ratchet wheel 14. When the rack 38 reaches an engaging position it engages the protruding portions 15p of the rotator/ratchet wheel 14 and rotates the rotator/ratchet wheel 14, which in turn rotates coupler 43. Coupler 43 engages or mates with a bone anchor screw 5, and rotation of the coupler 43 applies a torque on the bone anchor screw 5, thereby screwing it into bone.

Release of lever 4 by the operator transmits a compressive force through the force translator 12 (in this embodiment, a flexible wire) to the head assembly spring 39. A push force exerted by head assembly spring 39 in response to this compressive force forces the rack back into return groove 42 during the return stroke and disengages the rack 38 from the rotator 14.

The rack and rotator rotary force mechanism shown in FIG. 16 may also be adapted for a push embodiment. In a push embodiment, compressive loading on the force translator 12 forces the rack 38 forward to engage the rotator/ratchet wheel 14, which rotates in response to this engagement. The rotation of the rotator/ratchet wheel 14 rotates coupler 43, which in turn applies torque on a bone anchor screw 5. By varying the position of the connector 11 relative to the pivot 9 in the action mechanism as shown in FIGS. 18A and 18B, the device 36 may be configured to be used in either a pull or push embodiment.

Figure 17:
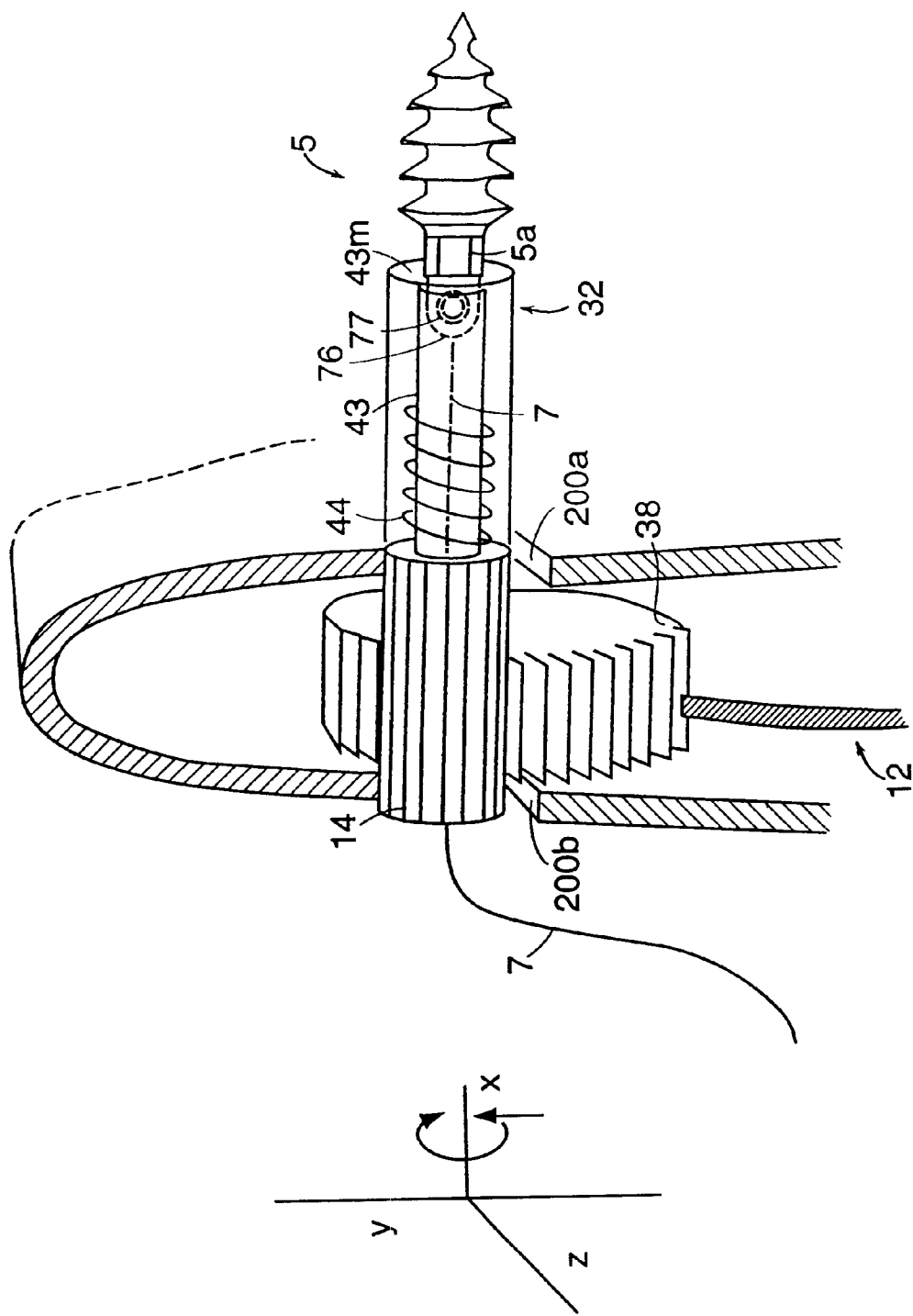
FIG. 17 shows an enlarged view of a head assembly in a rack and rotator manual bone anchor placement device in which the rotator comprises a pinion.

In the embodiment of the invention shown in FIG. 17, the rotator 14 is a pinion. Rotary motion from the rotator/pinion 14 is transmitted to a bone anchor screw 5 through coupler 43, which extends at least partially through the head end 3h of the shaft 3 through opening 200a. A push force or a pull force may be transmitted through the force translator 12, as discussed above, by varying the position of the connector 11 relative to the pivot 9 in the action mechanism of the device 36. A rotator spring 44 provides an opposing force to return the rotator/pinion 14 to its original position. In the embodiment of the invention shown in FIG. 17, the bone anchor screw 5 is pre-attached to a suture 7, and both the coupler 43 and the rotator/pinion 14 have openings through which the suture 7 is threaded. The suture 7 dangles from the head end 3h of shaft 3 through opening 200b.

Figure 19:
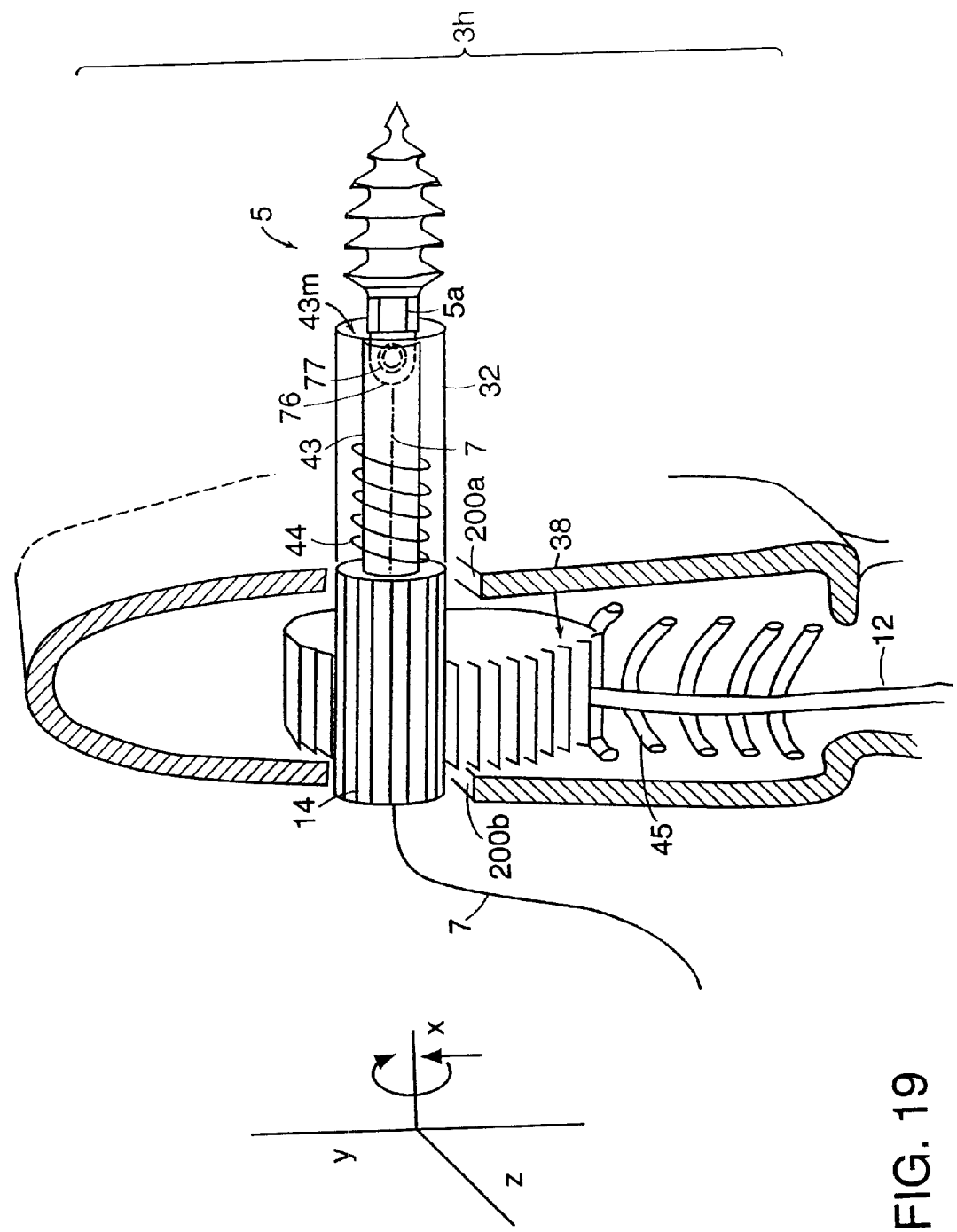
FIG. 19 shows an enlarged cross-sectional view of a head assembly in a rack and rotator manual bone anchor placement device according to one embodiment of the invention, in which linear force is transmitted to the rack through a rack spring and the rotator comprises a pinion. A bone anchor screw with a pre-attached suture is shown coupled to the pinion by a coupler. A protective cover covers the bone anchor screw. Dashed lines in the Figure show the portion of the bone anchor screw and pre-attached suture inside the coupler.

FIG. 19 shows an embodiment of the invention in which the rotator 14 is a pinion, and a compressive force, or push force, is transmitted on a force translator 12. An opposing compressive force is provided by rack spring 45, shown in cross-section in the Figure, that encircles the end of the force translator 12 proximal to rack 38 and forces the rack 38 back to its original position during a release stroke.

Figure 20:
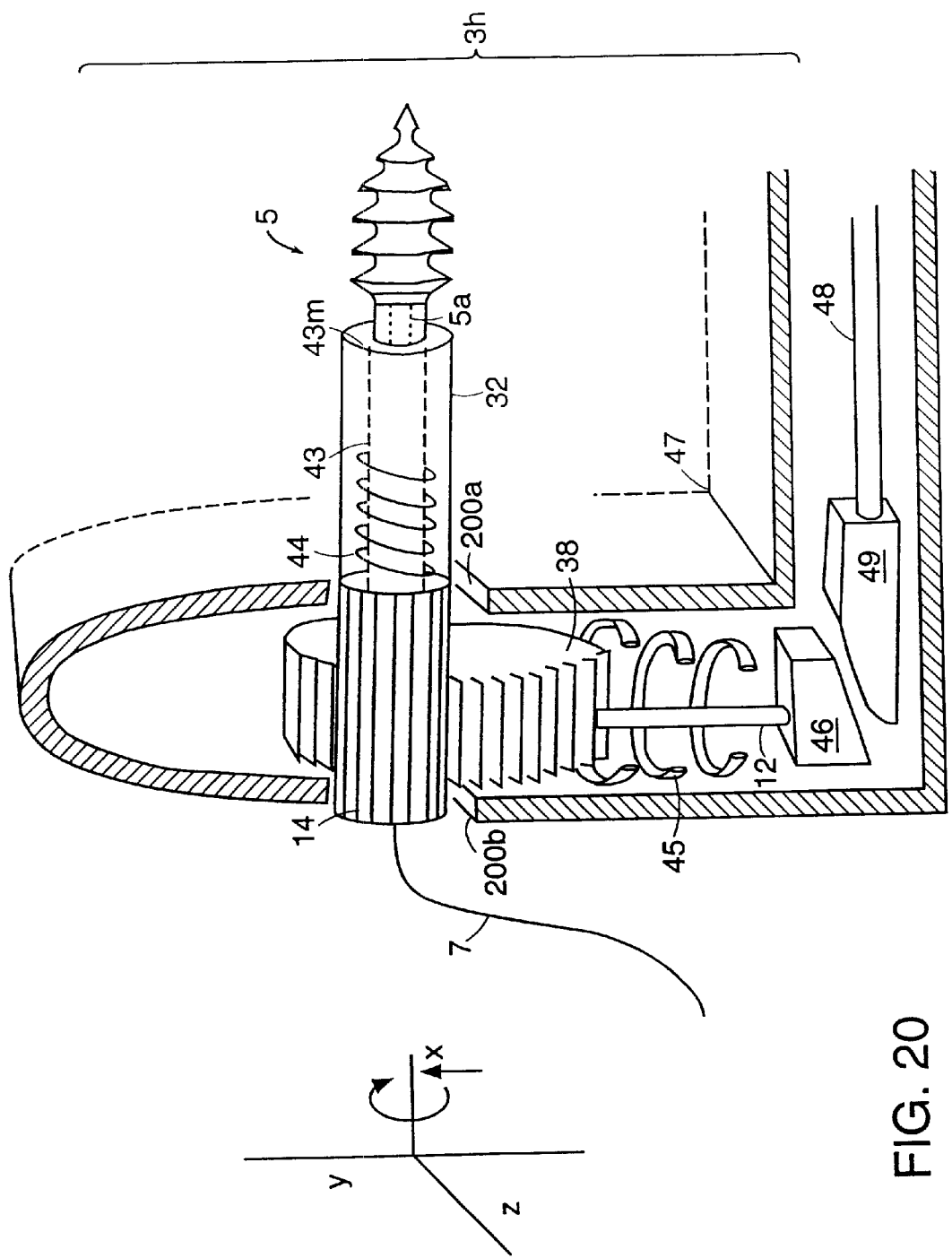
FIG. 20 shows an enlarged cross-sectional view of a head assembly in a rack and rotator manual bone anchor placement device according to one embodiment of the invention in which linear force is transmitted to the rack via wedge members.

FIG. 20 shows a further embodiment of the invention in which the force translator 12 includes a first wedge member 46 at the end of the force translator 12 distal to the rack 38. In this embodiment, the force translator 12 is not directly coupled to the lever 4, but terminates substantially at the neck 47 of the head end 3h of the shaft 3. The translator 12 receives force from a tubular member 48 that terminates in a second wedge member 49 and is connected to the lever 4 at connector 11. Actuation of the lever 4 pushes the second wedge member 49 against the first wedge member 46 and transmits a compressive force, i.e., a push force, to the force translator 12. During the release stroke, rotator spring 44 forces the rotator/pinion 14 back to its original position while rack spring 45 forces the rack 38 into its initial position.

Figure 21:
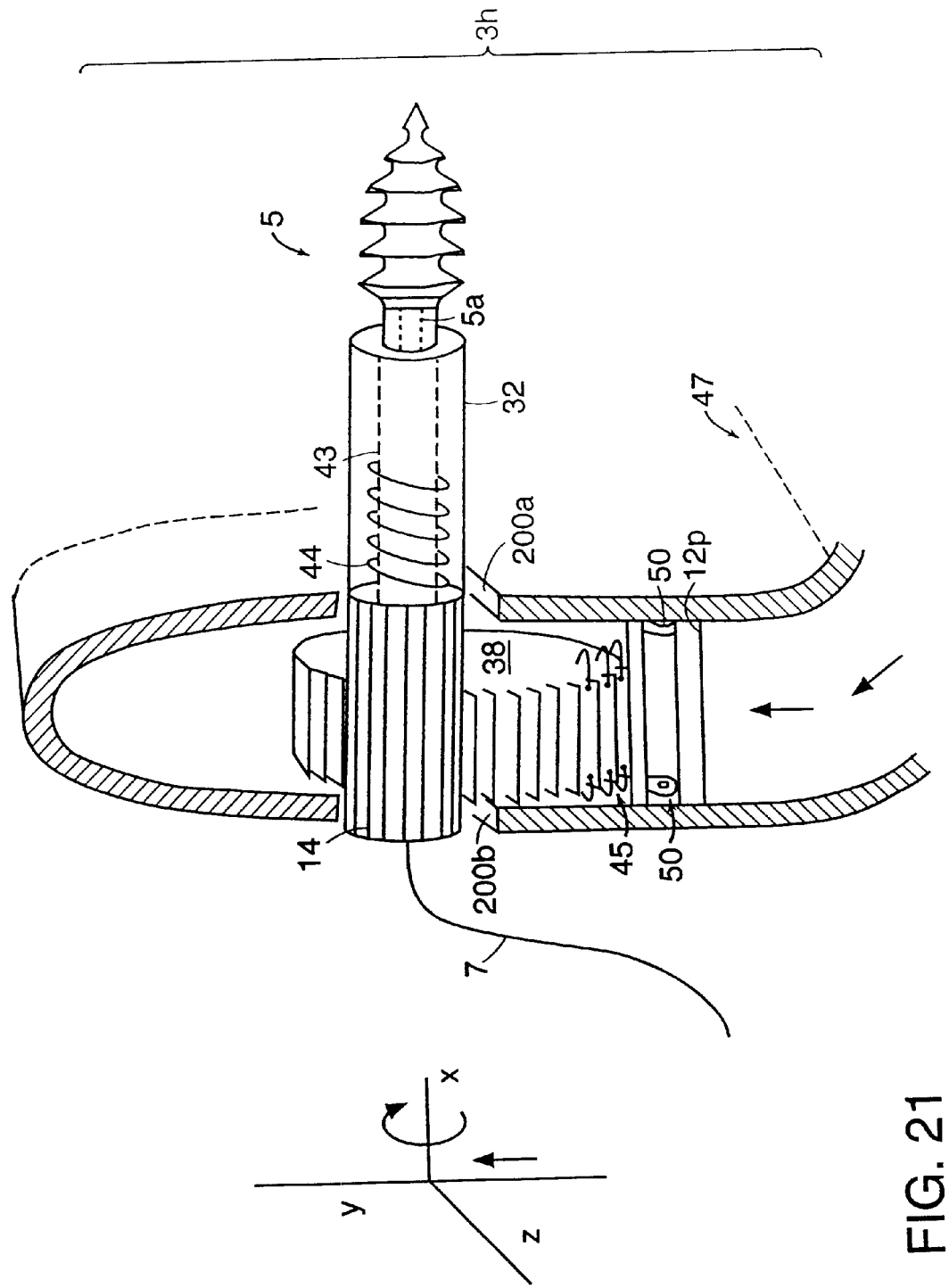
FIG. 21 shows an enlarged cross-sectional view of a head assembly in a rack and rotator manual bone anchor placement device according to one embodiment of the invention in which linear force is transmitted to the rack by pneumatic or hydraulic force on a plunger.

FIG. 21 shows a further embodiment of the invention in which hydraulic or pneumatic pressure is used to exert a compressive, or push force, on a force translator 12p. In this embodiment of the invention, the force translator 12p is a plunger positioned in close proximity to the rack 38. An o-ring 50 maintains a seal separating air or fluid in the shaft 3 from the rack 38 and rotator/pinion 14 assembly. Hydraulic or pneumatic forces transmitted through the shaft 3 upon actuation of the lever 4 drive the plunger 12p forward, transmitting linear force from the plunger 12p to the rack 38, which is in turn pushed forward to engage the rotator/pinion 14. The rotator/pinion 14 rotates and transmits rotary force to coupler 43, which applies a torque to a bone anchor screw 5. Opposing compression forces from rotator spring 44 forces the rotator/pinion 14 back to its original position while rack spring 45 forces the rack 38 to return to its initial position.

As will be readily apparent to those of ordinary skill in the art, many of the features of the wrap-around manual bone anchor placement device 1 may be adapted for use with the rack and rotator manual bone anchor placement device 36. For example, a suture 7 pre-attached to a bone anchor screw 5 may be clipped to the shaft 3 by suture rings 8 to keep the suture 7 from becoming entangled during the bone anchor screw 5 insertion procedure. Alternatively, the suture 7 may be enclosed within a flexible, molded sleeve 24 press-fitted into a groove 23 cut into the handle 2. A retaining clip 27 provided at the end of the sleeve 24 proximal to the gripping portion 26 of the handle 2 may be provided to prevent the suture 7 from slipping out of the sleeve 24 before the bone anchor screw 5 is screwed into bone.

Figure 5E:
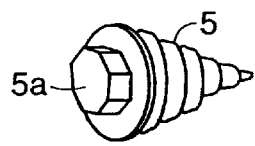
Figure 5F:
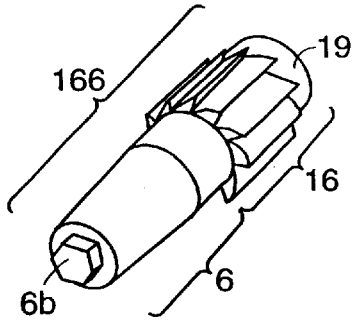
Figure 5G:
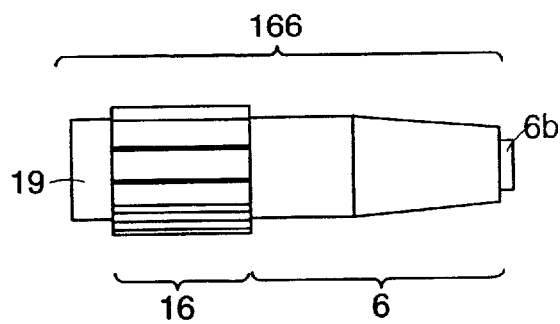
Figure 5H:
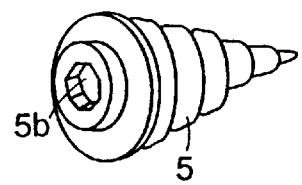

The coupler 43 may also be configured to be adapted to a wide variety of bone anchor screws 5. Like the securing element 166 of the wrap-around bone anchor placement device 1, the coupler 43 of the rack and rotator manual bone anchor placement device 36 includes a mating portion 43m that extends at least partially outside head end 3h of the shaft 3 and which can be fabricated to complement different types of bone anchor screws 5. In the embodiment of the invention shown in FIG. 19, the coupler 43 provides a mating portion 43m that is a hex-shaped recess that seats a bone anchor screw 5 with a hex-shaped shaft 5a, (e.g., as shown in FIG. 5E). The mating portion 43m of the coupler 43 may be configured in any type of shape (e.g., shaft or recess) that allows for frictional and mechanical engagement with a bone anchor screw 5 having the corresponding shape (e.g., recess or shaft).

As with the wrap-around manual bone anchor placement device 1, a protective cover 32 may be provided to protect the tip of the bone anchor screw 5 from damage before it contacts a bone insertion site, and may be collapsible to expose the bone anchor screw 5 only when it contacts the bone.

As with the wrap-around manual bone anchor placement device 1, the rack and rotator bone anchor placement device 36 may be fabricated in a modular configuration to provide for the ready interchange of different head modules and shaft modules. For example, a shaft 3 that has a rack and rotator head assembly 37 may be interchanged with a shaft 3 having the same type of head assembly 37, but with a different angle of curvature. Alternatively, a shaft 3 with a rack and rotator head assembly 37 may be interchanged with a shaft 3 having a wrap-around head assembly 35. Similarly, different couplers 43 may be interchanged to facilitate the use of different bone anchor screws 5.

Cup and Washer Manual Bone Anchor Placement Device

As with the previously disclosed manual bone anchor placement devices 1 and 36, the cup and washer manual bone anchor placement device 52, is configured to be substantially pistol- or gun-shaped, having a handle 2 with a gripping portion 26 and a lever 4. In the cup and washer manual bone anchor placement device 52, however, the "barrel of the gun" is formed by a driver rod 53 that extends through the handle 2 and is substantially perpendicular along its length to the longitudinal axis of the gripping portion 26 of the handle 2.

Figure 22B:
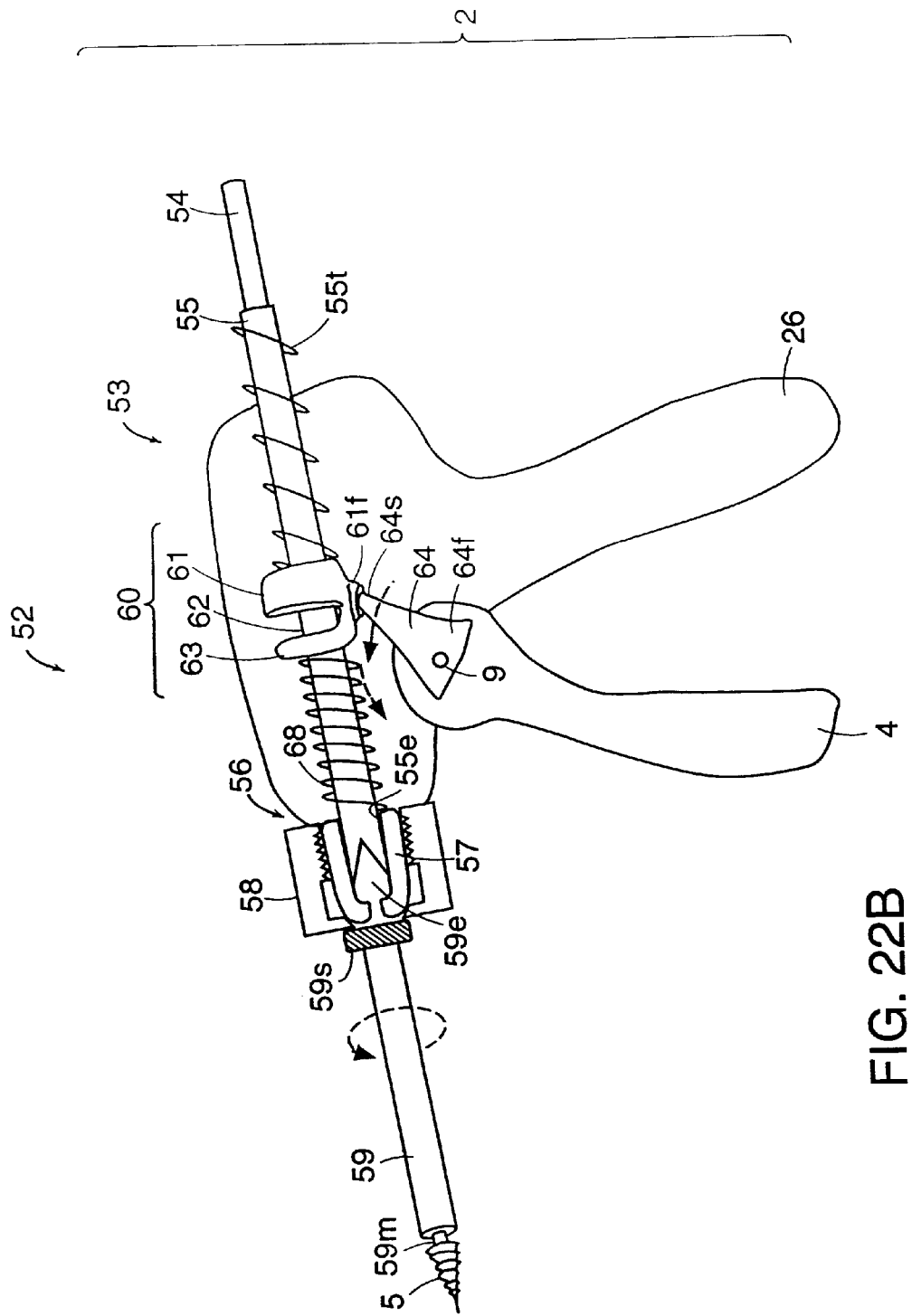
FIG. 22B shows a further embodiment of the invention in which a return coil spring is provided between the cup and washer assembly and the barrel end of the handle.
Figure 23A:
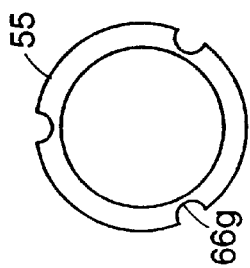
FIGS. 23A–23D show enlarged views of a cup and washer assembly used in a cup and washer manual bone anchor placement device according to one embodiment of the invention.
Figure 23B:
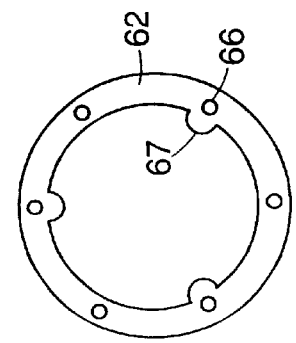
Figure 23C:
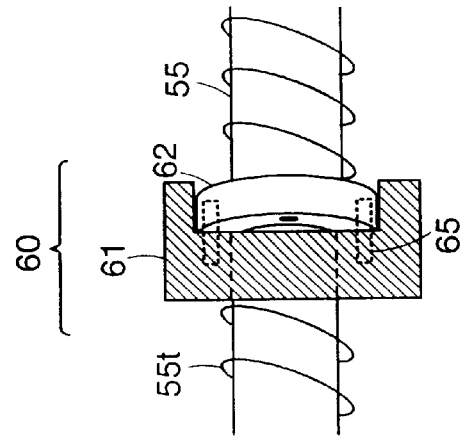
Figure 23D:
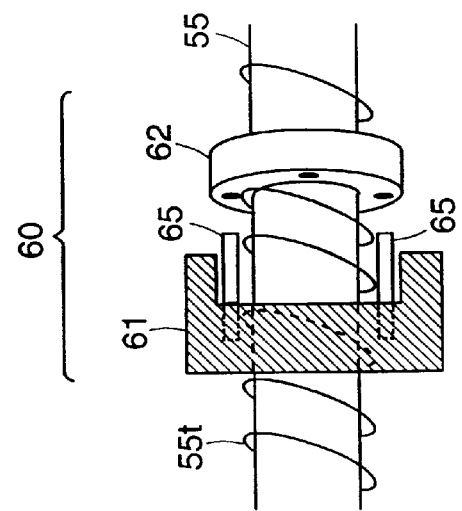

FIGS. 22A and 22B show a cross-section of the cup and washer manual bone anchor placement device 52. The driver rod 53 includes a smooth portion 54 and a lead screw portion 55 with integral single or multistart threads 55t. The lead screw portion 55 may be integral with the smooth portion 54. Alternatively, the lead screw portion 55 may be screwed onto threads or grooves at one of the ends of the smooth portion 52. The lead screw portion 55 may extend from one end of the handle 2 to the other end of the handle 2 or the lead screw portion 55 may comprise a substantial portion of the driver rod 53. As used herein, "a substantial portion" refers to greater than 50% of the length of the driver rod 53. In a different embodiment of the invention, the driver rod 53 may be flat stock twisted into a spiral with a long pitch.

The lead screw portion 55 of the driver rod 53 further includes an engaging element 55e at the end of the lead screw portion 55 distal to smooth portion 52 of the driver rod 53. The engaging element 55e engages with a coupling member 59. The coupling member 59 has a mating portion 59m for mating with a bone anchor screw 5 and an engaging portion 59e for engaging with the engaging element 55e of the lead screw portion 55.

The position of the coupling member 59 relative to the lead screw portion 55 of the driver rod 53 may be controlled by means of a coupling member stop 59s. A chuck 57 provided at the barrel end 56 of the handle 2 further secures coupling member 59 to the lead screw portion 55 of the driver rod 53. Since the chuck 57 contacts both the lead screw portion 55 of the driver rod 53 and the coupling member 59, any force transmitted through the driver rod 53 is also transmitted through the coupling member 59 to the bone anchor screw 5. In a further embodiment of the invention, a rotatable twist lock 58 is provided, thereby supplying an additional means of securing the chuck 57 to coupling member 59.

The rotary force mechanism in the cup and washer manual bone anchor placement device 52 includes cup and washer assembly 60, which includes a cup 61, a washer 62, and at least one engaging pin 65. The cup 61 is capable of axial movement along the lead screw portion 55 of the driver rod 53, while the washer 62 is capable of both axial motion and rotational motion along the lead screw portion 55.

Movement of the cup 61 is controlled by actuation of an action mechanism that includes a lever 4 and a force-translating member 64. The force-translating member 64 has a first end 64f and a second end 64s. The first end 64f of the force-translating member 64 is coupled to the lever 4 at pivot point 9 while the second end 64s is coupled to the side of the cup 61 by means of flanges 61f on the cup. The flanges 61f form a yoke that links the cup 61 to the force-translating member 64. The cup 61 is thus free to ride on the lead screw 55 in response to movement of force translating member 64.

The cup and washer manual bone anchor placement device 52 operates on the principle of a child's top. Applying a linear force on the lever 4 by squeezing it towards the gripping portion 26 of the handle 2 actuates the action mechanism. Linear force is transmitted from the lever 4 to the force-translating member 64 and is transmitted to cup 61.

Figure 24A:
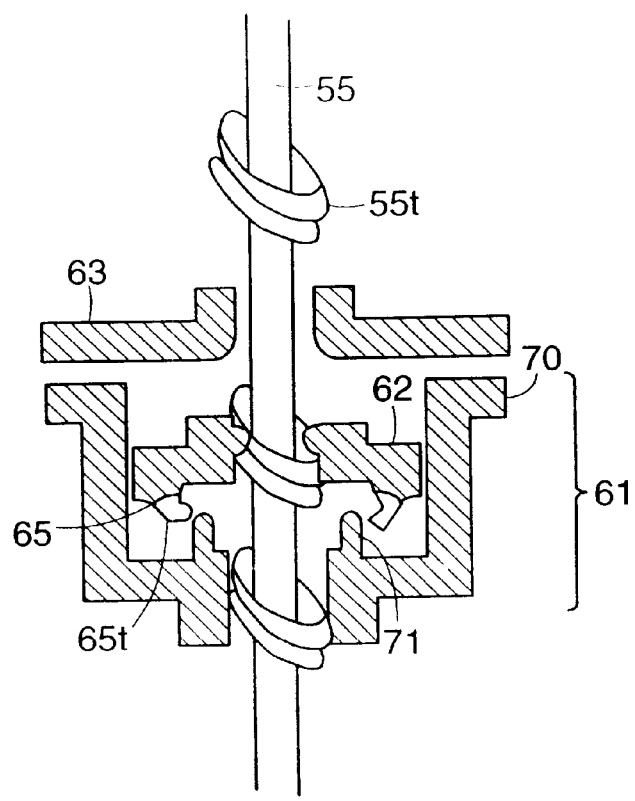
FIGS. 24A and 24B show enlarged views of a cup and washer assembly according to one aspect of the invention.
Figure 24B:
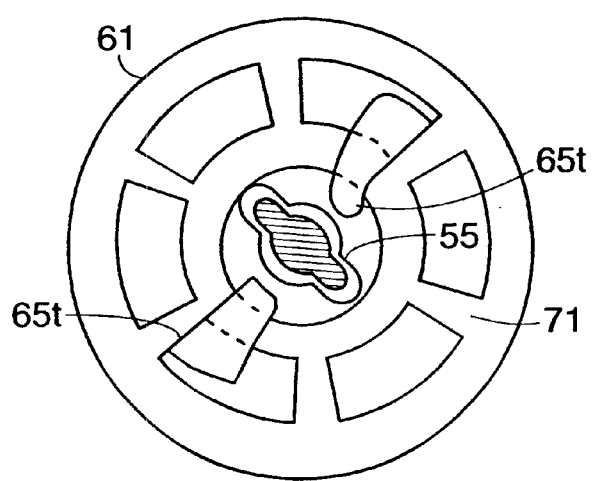
Figure 25A:
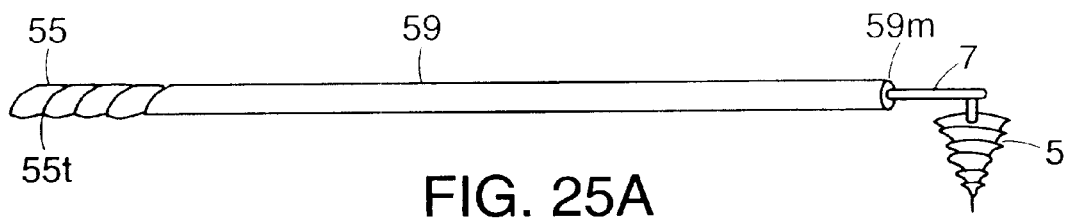
FIG. 25A shows a section of a lead anchor screw and a coupling element used in a cup and washer manual bone anchor placement device according to one embodiment of the invention in which the coupling element has a recess through which the suture of a bone anchor screw is threaded. The Figure shows the suture partly pulled out of the recess.
Figure 25B:
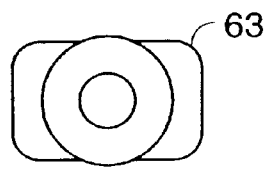
FIG. 25B shows a perspective view of the top of a cover plate used in a cup and washer assembly according to one embodiment of the invention.
Figure 25C:
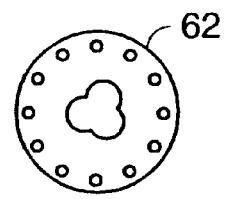
FIG. 25C shows a perspective view of the top of a washer used in a cup and washer assembly.
Figure 25D:
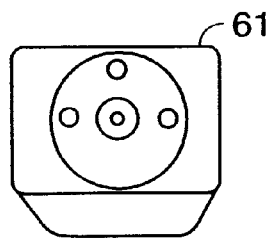
FIG. 25D shows a perspective view of the top of a cup used in the cup and washer assembly (i.e., the side that faces the washer).

In the embodiment of the invention shown in FIG. 23, the cup 61 has two engaging pins 65 that fit into complementary holes 66 in the washer 62. The cup 61 is capable of engaging and disengaging the washer 62 depending upon its direction of travel, while the washer 62 includes protrusions 67 that allow it to move along and follow the thread pitch of the threads 55t of the lead screw portion 55 of the driver rod 53. In the embodiment of the invention shown in FIG. 23A, the lead screw portion 55 includes grooves 66g complementary to protrusions 67 in the washer 62. In the embodiment of the invention shown in FIGS. 24A and 24B, the engaging pins 65 of the washer 62 further include tangs 65t, and the cup 61 includes ribs 71 that constrain the motion of the washer 62 further when the tangs 65t of the washer 62 contact the walls of the ribs 71.

Upon squeezing the lever 4, the translating member 64 is driven forward, moving the cup 61 forward at the same time (see dashed arrows in FIGS. 22A and B). When the motion of the cup 61 is initiated, the washer 62 is forced by the lead screw portion threads 55t into contact with the cup 61. The engagement pins 65 of the cup 61 then engage with the washer 62. Once engaged, the washer 62 is no longer free to rotate or spin on the lead screw portion threads 55t. As the translational member 64, cup 61, and washer 62, advance in a linear, forward direction, linear force from the force translating member 64 on the cup 61 is translated into rotary force upon the lead screw portion 55 of the driver rod 53, causing the driver rod 53 and the coupling member 59, which is coupled to it, to twist as the washer 62 follows the threads 55t of the lead screw portion 55. This twisting motion in turn applies a torque to a bone anchor screw 5 engaged by the coupling member 59, thereby screwing the bone anchor screw 5 into bone.

On the lever return stroke, there is minimal linear force imposed upon the coupling member 59. The cup 61 provides the washer 62 with clearance to disengage from the engaging pins 65 of the cup 61 and to rotate freely as the washer 62 follows the threads 55t on the lead screw portion 55 of the driver rod 53. In a further embodiment of the invention, shown in FIG. 22B, a return coil spring 68 may provided at the barrel end 56 of the handle 2 to further apply a return compressive force on the cup 61 and translating member 64 when the lever 4 is released.

By incorporating a 60-degree pitch angle and 3-start thread, the complete seating of a bone anchor screw 5 can take place in approximately 10 strokes of the lever 4. Optimizing thread 55t design, lever 4 stroke and/or cup 61/washer 62 clearance can reduce the number of strokes.

It should be readily apparent to one of ordinary skill in the art that the engaging pins 65 may be provided on the washer 62 side rather than the cup 61 side and that the holes 66 may be provided in the cup 61. The number of engagement pins 65 may also be varied. The engaging pins 65 may be an integral part of the washer 62 or cup 61, or may be removable from the washer 62 or cup 61. In addition, the number of starts in the multistart thread 55t of the lead screw portion 55 of the driver rod 53 may be varied from one through what ever number is dimensionally practical for the driver rod 53 diameter.

In a further embodiment of the invention as shown in FIGS. 22A, 22B, 24A, and 25B, a cover plate 63 is provided at the rim 69 of the cup 61 to contain the washer 62 within the cup 61 and to permit only minimal travel space for the washer 62 to move in when it is drawn free from the engaging pins 65 of the cup 61.

As with the previously disclosed manual bone anchor placement devices 1 and 36, the cup and washer manual bone anchor placement device 52 may be used with a bone anchor screw 5 with a pre-attached suture 7 that may be enclosed within a sleeve 24 press-fitted into a groove 23 cut into handle portion 2. The mating portion 59m of the coupling member may be configured to mate with a variety of bone anchor screws 5, and may include a shaft configured in a shape complementary to a recess in a bone anchor screw 5 or may include a recess complementary to a shaft in a bone anchor screw 5. As in the previously disclosed devices 1 and 36, the cup and washer manual bone anchor placement device 52 may include a modular design allowing for the interchange of different types of coupling members 59. The handle portion 2 may also be configured to include two separable halves that are able to snap-fit together, allowing removal of one driver rod and/or cup and washer assembly and replacement with another.

Self-Tapping Bone Anchor Screw

Figure 26:
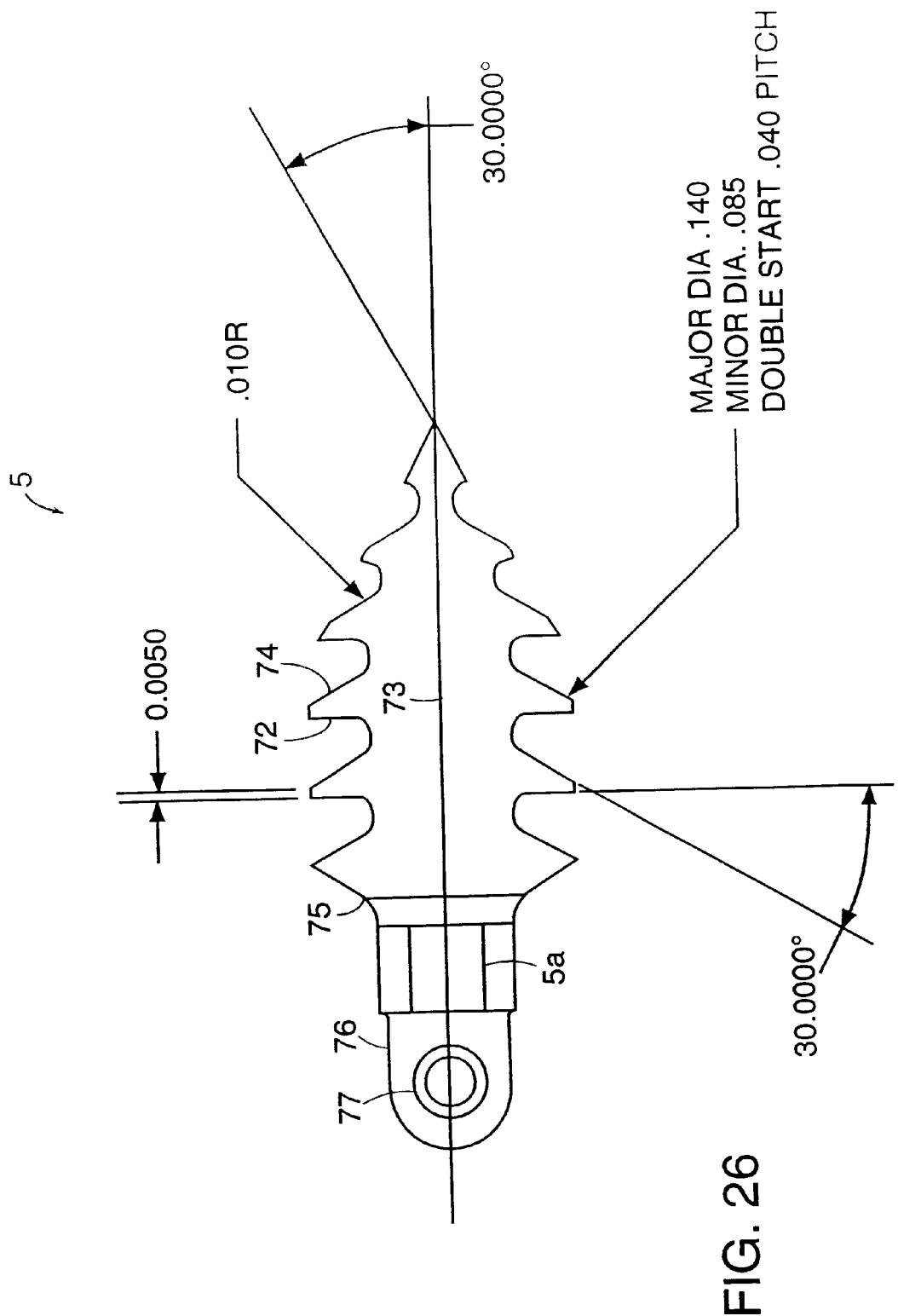
FIG. 26 shows a cross-section through a longitudinal axis of a self-tapping bone anchor screw according to one embodiment of the invention.

FIG. 26 shows a bone anchor screw 5 according to one embodiment of the invention. As shown in the FIG. 26, the threads of the bone anchor screw 5 are of buttress form. The forward face 72 of the screw thread is perpendicular to the longitudinal axis 73 of the bone anchor screw 5 while the back face 74 of the screw thread is at an acute angle relative to the longitudinal axis 73 of the bone anchor screw 5. The threads extend to the tip of the screw shank 75, reducing the amount of torque required to seat the bone anchor screw 5. In one embodiment of the invention, the back face 74 of the screw thread is at about a 30-degree angle relative to forward face 72 of the screw thread.

The base 76 of the bone anchor screw 5 shown in FIG. 26A has an eyelet 77 that is circular and has micropolished edges. In another embodiment of the invention, the eyelet 77 at base 76 may be teardrop shaped, or ellipsoidal. Other configurations may be used so long as the edges are rounded so as not to damage the suture 7. Micropolishing the eyelet 77 rounds the edges and reduces load to the suture 7 that may be caused by twisting (torsional load) during insertion, the user tugging on the suture 7 to test seating of the screw, and bodily movement while the anchor screw and suture are in place.

According to a further embodiment of the invention, kits including the disclosed self-tapping bone anchor screw may be provided for the convenience of the user. In one embodiment of the invention, a kit is provided, including at least one of: 1) a flexible, molded sleeve 24 for enclosing a suture 7, 2) a retaining clip 27 for preventing the suture 7 from slipping out of the sleeve 24, 3) a buttress-shaped bone anchor screw 5 with a micropolished eyelet 77 for receiving the suture 7, and 4) suture material, which may or may not, be pre-attached to the bone anchor screw 5. The kit may include any one of these elements or combinations thereof.

Recessed Bone Anchor Mount

The recessed bone anchor mount is designed to be used in conjunction with the various bone anchor placement devices described hereinabove; however, the recessed mount is not limited to use with only those types of bone anchor placement devices.

FIG. 27A is a perspective view of one embodiment of a bone anchor placement device 210 constructed according to the present invention. The anchor placement device 210 includes a handle 212, and a shaft 214 extending in a distal direction from the handle 212. A head assembly 216 is disposed at a distal end 218 of the shaft 214, and defines a core 220 that may be further defined by driver guide 300. A recessed anchor mount 222 is fixedly engaged within the core 220. In one embodiment, the handle 212 includes an actuator 224 for actuating a mechanism 226 for advancing or retracting the anchor mount 222.

The handle 212 serves as a gripping area for a surgeon, and is preferably of a size that makes it easily grippable by a user. A handle that is at least about 4 inches (100 mm) in length has been found to work well. The handle 212 may be made of any relatively firm material, including plastic or metal. For example, the handle 212 may be made of plastic, aluminum, stainless steel, or titanium. Those skilled in the art will appreciate that a wide range of other materials may also be employed. The handle 212 may be configured in any of a variety of shapes compatible with vaginal insertion of the anchor placement device 210. In the embodiment shown in FIG. 27A, the handle 212 tapers towards the proximal end to facilitate gripping by the user. Preferably, the handle 212 is provided with knurling or other surface texturing to produce a high friction, non-slip gripping surface.

The shaft 214 extends in a distal direction from the handle 212, and is adapted for releasably engaging a bone anchor 230. The shaft 214 has a distal end 218, and a proximal end 228. The shaft 214 may be curved or angled at one or more portions to facilitate correct placement of the bone anchor placement device 210 to a proper bone anchor insertion site. The shaft 214 may be made of any of a variety of materials; including steel, stainless steel, aluminum, titanium, and plastic, but is preferably made of stainless steel. The shaft 214 may have a variety of cross-sectional shapes including round, elliptical, rectangular, hexagonal, or triangular, but preferably the shaft 214 has a round cross-section.

The length of the shaft 214 is consistent with transvaginal delivery of a releasable bone anchor 230 and may be of an appropriate length to permit access of the bone anchor 230 to the desired location. The cross-sectional dimension of the shaft 14 is a function of the force-translating mechanism (variations of which are described hereinabove) and the actuator mechanism 226 and may range from about 0.2 to about 1.0 inch in diameter.

Figure 28A:
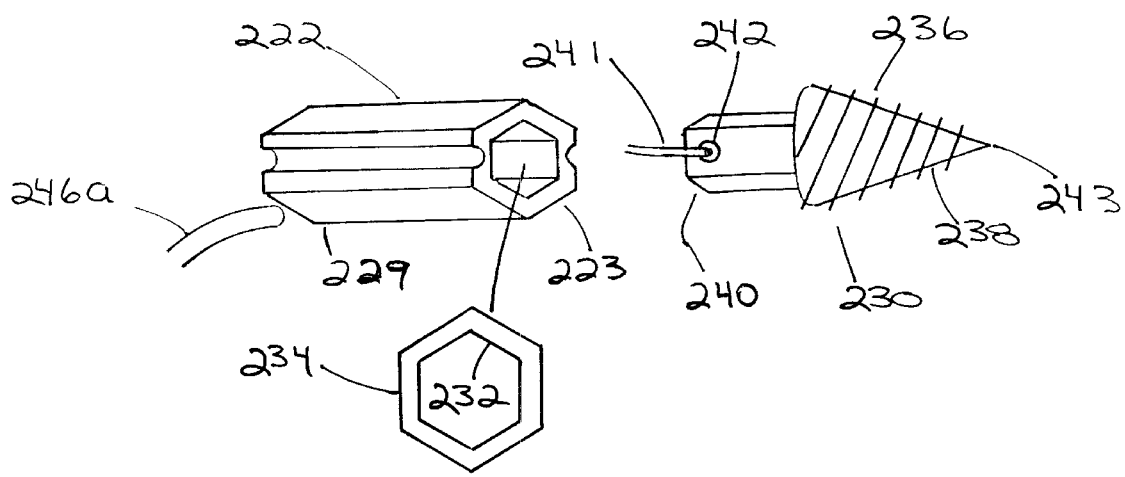
FIG. 28A is an enlarged perspective view of one embodiment of an anchor mount constructed according to the present invention and of a bone anchor for attachment to the anchor mount.
Figure 28B:
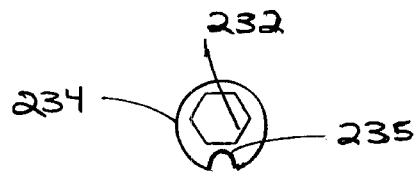
FIGS. 28B and 28C are end views of alternate embodiments of an anchor mount constructed according to the present invention.
Figure 28C:
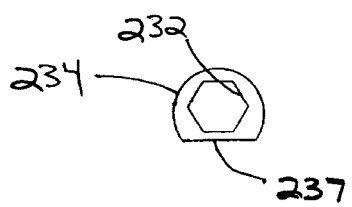

FIG. 28A is an enlarged view of one embodiment of a recessed anchor mount 222 constructed according to the present invention and of a bone anchor 230 for attachment to the anchor mount 222. The mount 222 has a distal end 223 and a proximal end 229. In one embodiment, the mount 222 has a hexagonal interior lumen 232, and a matching or complimentary outer surface 234. The mount 222 may have other configurations for its interior lumen 232 and outer surface 234, such as a rectangular, pentagonal, octagonal, or round. FIG. 28B depicts an end view of an alternative anchor mount 222 with a primarily round outer surface 234 and a groove 235 for interlocking with a pin or protuberance (not shown) within the driver guide 300. FIG. 28C depicts an end view of an alternative anchor mount 222 with a primarily round outer surface 234 and a flat surface 237 for interlocking with a mating flat surface (not shown) within the driver guide 300.

A variety of bone anchors 230 can be used. In one embodiment, the bone anchor 230 includes a spear member 236 that is able to pierce and securely engage a bone or bone tissue. The spear member 36 has a generally cone shaped head portion 238 which is used to pierce the bone and a shaft portion 240 with an eyelet 242 therethrough for receiving and holding one or more suture strands 241.

The outer surface of the shaft portion 240 of the anchor 230 is shaped to fit within the anchor mount 222, and is adapted to rotate with the anchor mount 222. In preferred embodiments, the shaft portion 240 has the eyelet 242 formed radially therethrough proximate one of its ends. The eyelet 242 may be of any shape and is of a sufficient size to permit a suture strand or strands 241 to pass therethrough. The circumference of each outer end of the eyelet 242 is preferably chamfered or grounded to provide a beveled surface. A beveled surface provides a generally smooth surface for contacting a suture strand 41 that has been passed through the eyelet 242. The eyelet 242 is preferably located on the shaft portion 240 of the anchor 230 such that the transverse axis of the eyelet 242 intersects the longitudinal axis of the spear member 236.

The generally cone-shaped head portion 238 of the spear member 236 is located at an end of the shaft portion 240 opposite the end having the eyelet 242. The apex of the cone-shaped head portion may terminate in a sharp tip or point 243 that is suitable for being driven into bone. The diameter of the cone-shaped head portion 238 increases, when viewed along its longitudinal direction rearwardly from the point 243, towards the shaft portion 240.

Any known materials suitable for orthopedic anchor devices may be employed to construct the bone anchor 230 of the present invention. Preferably, the bone anchor 230 is formed from a plastic polymer or metallic material possessing sufficient strength to penetrate and anchor to bone. Such materials include titanium, 316 LVM stainless steel, CoCrMo alloy, Nitinol alloy, or polymers, for example, polyglycolic acid (PGA) with or without absorbability properties. Preferably, the bone anchor is made of titanium.

Figure 29A:
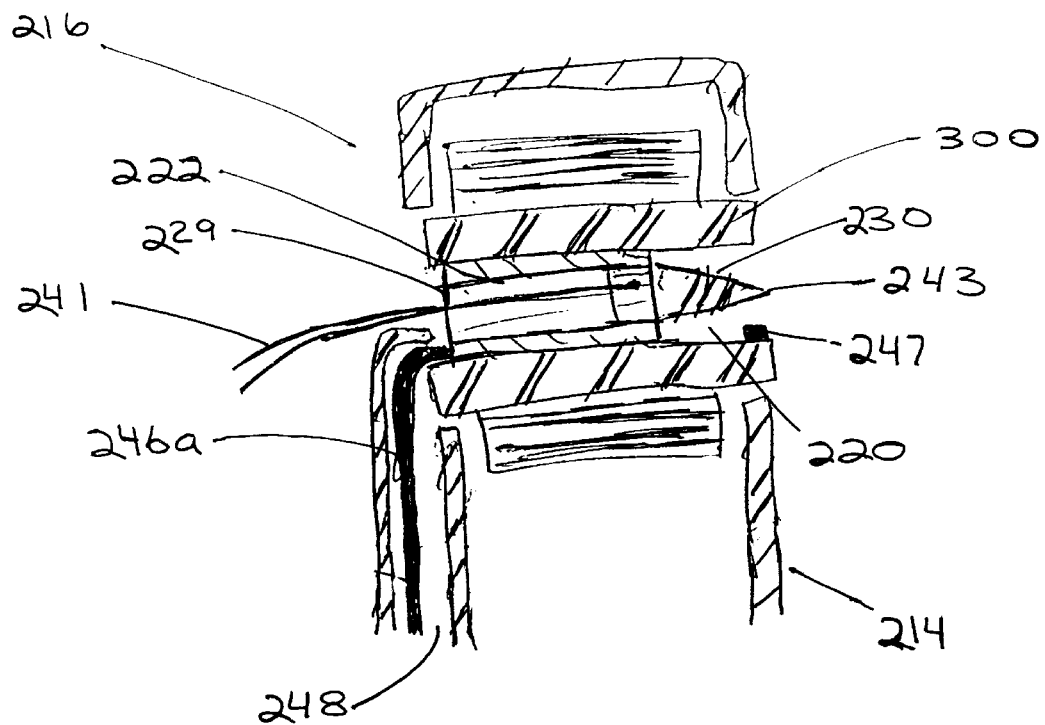
FIG. 29A is an enlarged view of one embodiment of the head assembly of the anchor placement device of FIG. 27A, and of a recessed anchor mount in a recessed position within the head assembly.

FIG. 29A is an enlarged view of one embodiment of the head assembly 216 of the anchor placement device 210 of FIG. 27A, and a recessed anchor mount 222 housed within the head assembly 216 in a retracted position.

The head assembly 216 is capable of releasably engaging a bone anchor mount 222 and is connected to a mechanism 226 that translates axial motion to the mount 222 to advance or retract the anchor 230. The head assembly 216 defines a hollow core 220 that may be further defined by driver guide 300. The interior dimensions of the core 220, or driver guide 300, permit a recessed anchor mount 222 to be moveably fitted therein. In preferred embodiments, the interior dimensions of the core 220, or driver guide 300, are only slightly larger than the exterior dimensions of the anchor mount 222. The length of the anchor mount 222 is about 0.12 to about 0.25 inches, preferably about 0.15 to about 0.20 inches, and more preferably about 0.185 inches. The length of the driver guide 300 is essentially the length of the anchor mount 222 and the anchor 230.

In preferred embodiments, the core 220 has a shape complementary to the proximal end 229 of the anchor mount 222, so as to permit the mount 222 to engage the driver guide 300. For example, the driver guide 300 and the proximal end 229 of the anchor mount 222 may be square, rectangular, pentagonal, triangular or hexagonal in cross-section. In some embodiments, the driver guide 300 and the proximal end 229 of the anchor mount 222 have hexagonal cross-sections; however, those skilled in the art will appreciate that numerous shapes may be employed and the present invention specifically contemplates any such shape. In some embodiments, driver guide 300 includes a stop 247 disposed on the interior surface of the driver guide 300. In alternative embodiments, the stop is disposed on the mechanism 226 and limits the travel of the mechanism 226, and thereby limits the travel of the anchor mount 222. The stop 247 prevents driving the bone anchor 230 too far into the bone.

Figure 29C:
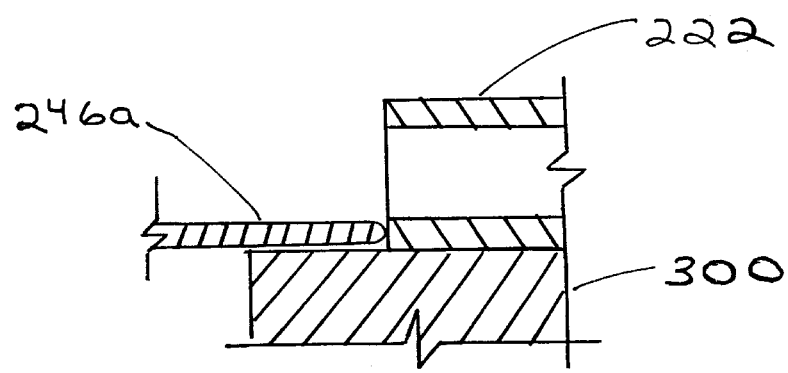
FIG. 29C is an enlarged view of a push wire in point contact with the anchor mount of FIG. 29A
Figure 29D:
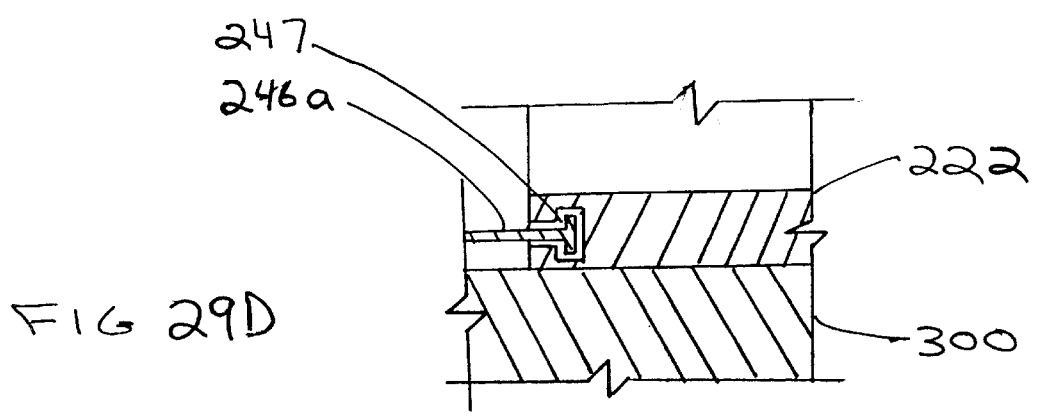
FIG. 29D is an enlarged view of a push wire secured to the anchor mount of FIG. 29A.
Figure 30A:
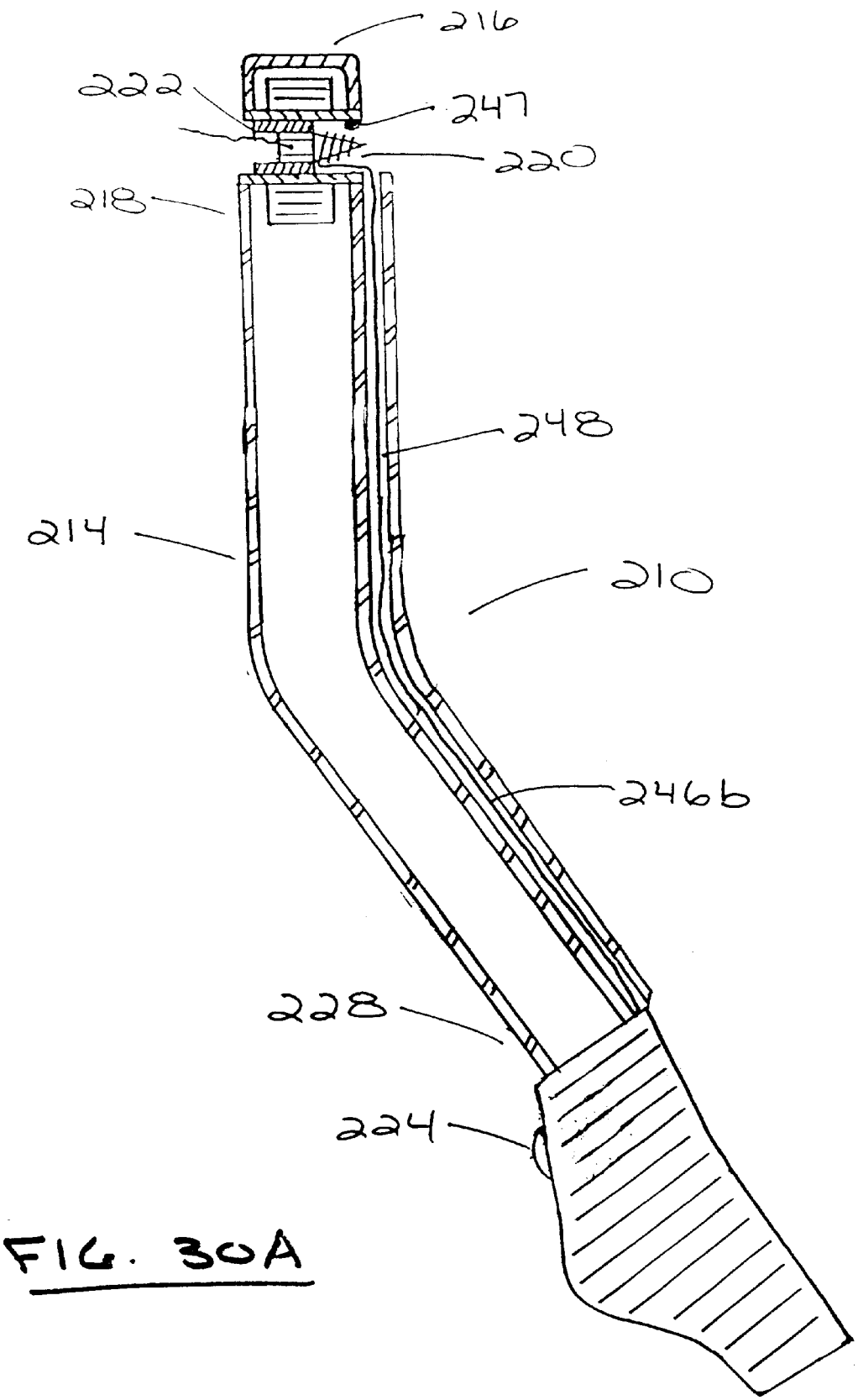
FIG. 30A is a side view of an alternate embodiment of the anchor placement device depicted in FIG. 27A.
Figure 30B:
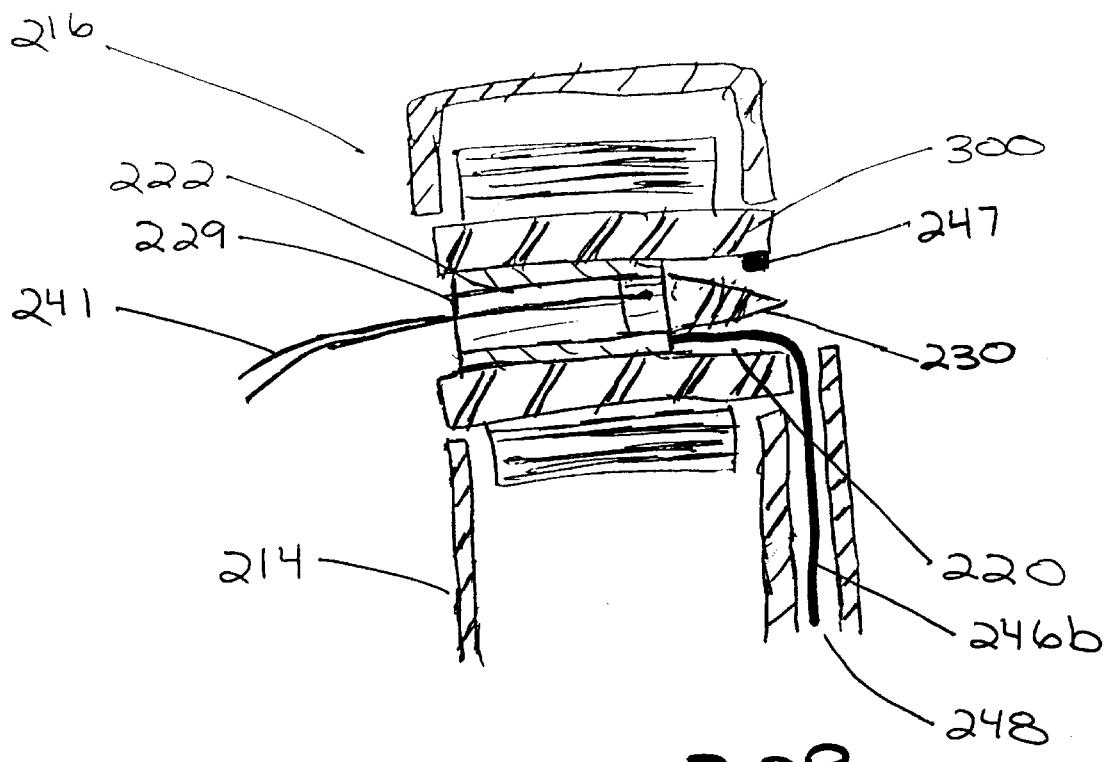
FIG. 30B is an enlarged view of one embodiment of the head assembly of the anchor placement device of FIG. 30A, and of a recessed anchor mount in a recessed position within the head assembly.

In some embodiments, the mechanism 226 that translates motion to the mount 222 is a push wire 246a. Alternatively, the mechanism 226 could be a pull wire 248b as depicted in FIGS. 30A and 30B. The mechanism 226 operates on the same principle whether a push wire 246a or a pull wire 246b is used, and the following description is directed only to a push wire 246a for simplicity. The push wire 246a is coupled to the anchor mount 222 via a point contact, as shown in FIG. 29C, to advance or retract the anchor mount 222. Alternatively, the push wire 246a may be secured to the anchor mount 222. For example, the push wire 246a may be welded or crimped to the anchor mount 222, in which case the push wire 246a must be able to twist and roll freely within the shaft 214. In such embodiments, the actuator to push wire connection is preferably non-fixed. In alternative embodiments, the push wire 246a may be coupled to the anchor mount 222 via a free-floating mechanism 247, as shown in FIG. 29D.

As shown in FIGS. 27A and 30A, the push/pull wire 246a,b is a substantially linear member that extends from the handle 212. The push/pull wire 246a,b is made of a high tensile material. Suitable push wire materials include metals, plastics, and reinforced polymers. In preferred embodiments, the push/pull wire 246a,b is made of spring steel, or superelastic nitinol. In some embodiments, a groove or channel 248 is cut into the outer surface of the shaft 214, extending in a line substantially parallel to the longitudinal axis of the shaft 214. Alternatively, the groove or channel may be otherwise formed as part of the shaft 14 and may completely encapsulate the push/pull wire 246a,b and/or mechanism 226, for examples see FIGS. 27B–27E. The push/pull wire 246a,b is situated within the channel 248 disposed on the shaft 214. In some embodiments, an actuator 224, such as a button, lever, or trigger disposed on the handle 212, activates the push/pull wire 246a,b. Force exerted on the actuator 224 is translated to the anchor mount 222 as linear force through the push/pull wire 246a,b.

During insertion of the device 210 into the body, the anchor mount 222, as well as an attached bone anchor 230, remain in a recessed position, as shown in FIG. 29A. The sharp tip 243 of the anchor 230 therefore remains unexposed to bodily tissue. The likelihood of tearing and scraping of tissue, as well as injury to delicate abdominal organs, is thereby reduced. Because the bone anchor 230 remains protected within the hollow core 220 of the head assembly 216, the likelihood of dislodgment of the bone anchor 230 during insertion is also reduced. The need for protective covers or sheaths for the purpose of shielding the tip 243 of the anchor is also reduced. Furthermore, when the anchor mount 222 is recessed, the profile of the head assembly 216 is reduced in comparison to the configuration where the anchor mount 222 protrudes from the head assembly 216. Therefore, a smaller vaginal incision is required, as compared to the situation where a protective shroud or cover is provided for the bone anchor 230.

Figure 29B:
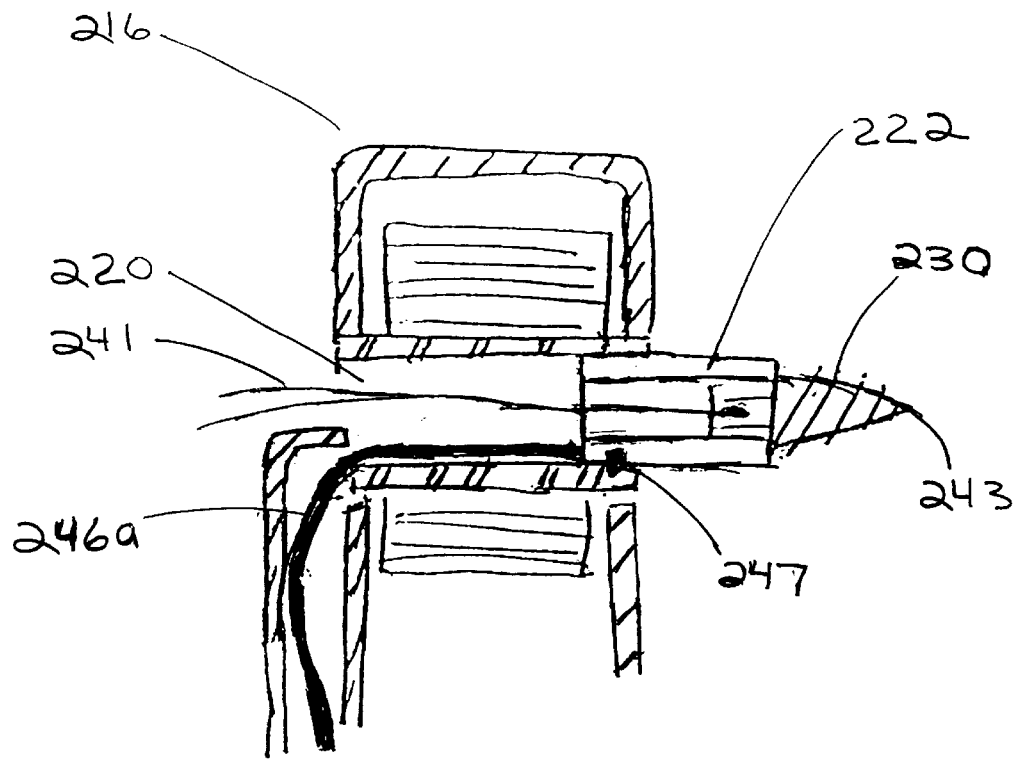
FIG. 29B is an enlarged view of one embodiment of the head assembly of the anchor placement device of FIG. 27A, and of a recessed anchor mount in an advanced position protruding from the head assembly.

FIG. 29B is an enlarged view of one embodiment of a head assembly 216 of an anchor placement device 210 of FIG. 27A, and a recessed anchor mount 222 protruding from the head assembly 216.

In operation, when a force is exerted on the actuator 224 by pushing, pulling, or otherwise actuating the actuator 224, the exerted force is translated as a linear force through the push/pull wire 246a,b to the anchor mount 222. Optionally, the actuator 224 can be locked in place to prevent the anchor mount 222 from retracting. As the exerted linear force is transmitted to the anchor mount 222 through the push/pull wire 246a,b, the anchor mount 222 advances linearly, moving within the driver guide 300. The attached bone anchor 230 may advance with the anchor mount 222 until halted by the optional stop 247 disposed within the driver guide 300. In an alternative embodiment, the mechanism 226 may also actuate a force-translating mechanism (variations of which are described hereinabove), and thereby turn the anchor mount 222 in response to the applied force.

Having thus described certain embodiments of the present invention, various alterations, modifications, and improvements will be obvious to those skilled in the art. Such variations, modifications and improvements are intended to be within the spirit and scope of the invention. The materials employed, as well as their shapes and dimensions, generally can vary. Accordingly, the foregoing description is by way of example only and is not intended to be limiting.

What is claimed is:

1. A manual bone anchor placement device, comprising:

a handle;

a shaft extending in a distal direction from the handle;

a head assembly disposed at a distal end of the shaft;

a recessed anchor mount movably disposed within the head assembly; and an actuation mechanism coupled to the recessed anchor mount wherein the actuation mechanism is selected from the group consisting of a push wire and a pull wire.

2. The manual bone anchor placement device of claim 1, wherein the actuation mechanism actuates the recessed anchor mount between a recessed position and an advanced position.

3. The manual bone anchor placement device of claim 1, wherein the anchor mount includes an outer surface comprising at least one flat surface and the head assembly defines a core comprising a mating shape.

4. The manual bone anchor placement device of claim 1, wherein the actuation mechanism is situated within a channel disposed on the handle.

5. The manual bone anchor placement device of claim 4, wherein an actuator operates the actuation mechanism disposed on the handle.

6. The manual bone anchor placement device of claim 1, wherein the actuation mechanism comprises a material selected from the group consisting of spring steel and nitinol.

7. The manual bone anchor placement device of claim 1 further comprising a bone anchor releasably engaged to the anchor mount.

8. The manual bone anchor placement device of claim 1 further including a stop disposed within the head assembly.

* * * * *